United States Patent
Bharat et al.

(10) Patent No.: US 12,178,638 B2
(45) Date of Patent: Dec. 31, 2024

(54) BIOPSY PREDICTION AND GUIDANCE WITH ULTRASOUND IMAGING AND ASSOCIATED DEVICES, SYSTEMS, AND METHODS

(71) Applicant: KONINKLIJKE PHILIPS N.V., Eindhoven (NL)

(72) Inventors: Shyam Bharat, Arlington, MA (US); Grzegorz Andrzej Toporek, Boston, MA (US); Claudia Errico, Cambridge, MA (US); Marcin Arkadiusz Balicki, Cambridge, MA (US); Man Nguyen, Melrose, MA (US); Carolina Amador Carrascal, Everett, MA (US); Raghavendra Srinivasa Naidu, Auburndale, MA (US); Haibo Wang, Melrose, MA (US); Hua Xie, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 310 days.

(21) Appl. No.: 17/252,293

(22) PCT Filed: Jun. 28, 2019

(86) PCT No.: PCT/EP2019/067366
§ 371 (c)(1),
(2) Date: Dec. 15, 2020

(87) PCT Pub. No.: WO2020/002620
PCT Pub. Date: Jan. 2, 2020

(65) Prior Publication Data
US 2021/0259660 A1  Aug. 26, 2021

Related U.S. Application Data
(60) Provisional application No. 62/693,808, filed on Jul. 3, 2018, provisional application No. 62/691,688, filed on Jun. 29, 2018.

(51) Int. Cl.
*A61B 8/00* (2006.01)
*A61B 8/08* (2006.01)
*A61B 8/12* (2006.01)

(52) U.S. Cl.
CPC .............. *A61B 8/0841* (2013.01); *A61B 8/12* (2013.01); *A61B 8/463* (2013.01); *A61B 8/485* (2013.01); *A61B 8/488* (2013.01); *A61B 8/5207* (2013.01)

(58) Field of Classification Search
CPC ......... A61B 8/0841; A61B 8/12; A61B 8/463; A61B 8/485; A61B 8/488; A61B 8/5207; G06T 2207/20084
See application file for complete search history.

(56) References Cited

U.S. PATENT DOCUMENTS 5,260,871 A  11/1993  Goldberg
5,984,870 A *  11/1999  Giger .................... G06T 7/0012
                                                                    600/443

(Continued)

FOREIGN PATENT DOCUMENTS

JP       2017118921 A   7/2017
WO       9904680 A2     2/1999

(Continued)

OTHER PUBLICATIONS

Azizi S, Van Woudenberg N, Sojoudi S, Li M, Xu S and et al. "Toward a real-time system for temporal enhanced ultrasound-guided prostate biopsy." Int J Comput Assist Radiol Surg. 1201-1209. (Year: 2018).*

(Continued)

*Primary Examiner* — Amal Aly Farag

(57) ABSTRACT

Ultrasound image devices, systems, and methods are provided. An ultrasound imaging system includes a communication interface in communication with an ultrasound imaging device. The communication interface receives an (Continued)

ultrasound image of a subject's anatomy. The system includes a processor in communication with the communication interface. The processor applies a predictive network to the ultrasound image to identify a plurality of locations of potential malignancies in the subjects anatomy and determines a plurality of malignancy likelihoods at the plurality of locations of potential malignancies. The processor outputs, to a display in communication with the processor, the plurality of locations of potential malignancies and the plurality of malignancy likelihoods for the plurality of locations of potential malignancies to guide a biopsy determination for the subject's anatomy.

21 Claims, 12 Drawing Sheets

(56) References Cited

U.S. PATENT DOCUMENTS

| | | | |
|---|---|---|---|
| 6,058,322 A * | 5/2000 | Nishikawa | G06T 7/0012 382/128 |
| 2003/0135115 A1* | 7/2003 | Burdette | A61N 5/103 600/437 |
| 2006/0241451 A1* | 10/2006 | Nakaya | A61B 8/463 600/443 |
| 2008/0170770 A1 | 7/2008 | Suri et al. | |
| 2009/0137907 A1 | 5/2009 | Takimoto et al. | |
| 2010/0121178 A1 | 5/2010 | Krishnan et al. | |
| 2010/0292571 A1 | 11/2010 | Kim et al. | |
| 2014/0018699 A1* | 1/2014 | Rusnak | A61B 10/0266 600/566 |
| 2014/0094695 A1* | 4/2014 | Jain | A61B 8/481 600/424 |
| 2014/0142422 A1* | 5/2014 | Manzke | A61B 8/12 600/424 |
| 2014/0314292 A1* | 10/2014 | Kamen | G16H 30/20 435/29 |
| 2015/0366537 A1* | 12/2015 | Hashimoto | A61B 8/0841 600/440 |
| 2016/0314583 A1 | 10/2016 | Couch et al. | |
| 2016/0374644 A1 | 12/2016 | Mauldin et al. | |
| 2017/0150941 A1* | 6/2017 | Jago | A61B 8/5207 |
| 2018/0000465 A1* | 1/2018 | Brown | A61B 10/025 |
| 2018/0028261 A1 | 2/2018 | Chen et al. | |
| 2018/0075628 A1* | 3/2018 | Teare | G06F 18/24143 |
| 2018/0125446 A1 | 5/2018 | Boroczky et al. | |

FOREIGN PATENT DOCUMENTS

| | | | | |
|---|---|---|---|---|
| WO | 9904690 | A1 | 2/1999 | |
| WO | 2005001740 | A2 | 1/2005 | |
| WO | 2007137179 | A2 | 11/2007 | |
| WO | 2016103094 | A1 | 6/2016 | |
| WO | WO-2018094118 | A1 * | 5/2018 | A61B 8/12 |

OTHER PUBLICATIONS

PCT/EP2019/067366 ISR & WO, Oct. 4, 20219, 16 Page Document.

* cited by examiner

BIOPSY PREDICTION AND GUIDANCE WITH ULTRASOUND IMAGING AND ASSOCIATED DEVICES, SYSTEMS, AND METHODS

CROSS-REFERENCE TO PRIOR APPLICATIONS

This application is the U.S. National Phase application under 35 U.S.C. § 371 of International Application No. PCT/EP2019/067366, filed on Jun. 28, 2019, which claims the benefit of U.S. Provisional Patent Application No. 62/693,808, filed on Jul. 3, 2018 and U.S. Provisional Patent Application No. 62/691,688, filed on Jun. 29, 2018. These applications are hereby incorporated by reference herein.

TECHNICAL FIELD

The present disclosure relates generally to ultrasound imaging and, in particular, to providing automated systems and methods for guiding a biopsy.

BACKGROUND

Ultrasound has a prominent role in screening and diagnosing a number of conditions in different anatomies. Ultrasound is also often employed to guide biopsy procedures, from a biopsy needle guidance standpoint and also from a target identification standpoint. In the thyroid, for example, brightness-mode (B-mode) ultrasound features such as size, echogenicity, shape, calcifications, margins and presence or absence of a cystic component are used to classify a nodule as benign or malignant. Elasticity features may also be used in addition to B-mode ultrasound features.

A thyroid suspicious for malignancy often includes multiple biopsy candidate locations (e.g., multiple nodules, or multiple locations within a large nodule). The need for biopsy, along with the biopsy location, is typically identified by a clinician using the clinician's expertise in determining the level of suspicion for cancer in a given nodule and/or using an algorithm based on the size of the nodule that suggests whether a biopsy is indicated for that patient. For example, for a highly suspicious nodule, a biopsy is indicated for a nodule as small as about 1 centimeter (cm), but for a very low suspicion nodule, a biopsy is indicated for a nodule with a diameter greater than 2 cm. Once a biopsy location is identified, a needle can be advanced towards the target under ultrasound guidance.

A biopsy sample can be acquired using one of two techniques, a capillary technique or an aspiration technique. The capillary technique and the aspiration technique have similar workflows, but differ in how a sample is collected. Typically, a hollow needle with a bevel-shaped tip and a 10 cubic centimetre (cc) Luer Lock syringe are used. The length of the needle can be between about 1.25 inches to about 1.5 inches. The thickness of the needle can be between about 23 gauge (G) to about 27 G. Thicker needles (e.g., about 20 G or 22 G) can lead to patient trauma and/or blood contamination. Thus, needles that are at least about 24 G to about 25 G are recommended. In some instances, for deeper insertions and/or in patients with thicker necks, a solid stylet, which is shorter than a needle, can be inserted into a needle (e.g., a hollow needle) to provide support.

Since a thyroid suspicious for malignancy can include multiple biopsy candidate locations, it is left to the clinician to choose a preferred location. Additionally, it is clinically indicated to allow no more than n passes or attempts at a biopsy, where n may typically be about 5, to minimize patient trauma. The choice of biopsy location may also be based on proximity of the nodule and/or needle path to one of the many critical structures that surround the thyroid, such as the jugular vein, carotid artery, trachea and esophagus. As such, biopsies are often non-diagnostic or may have a reduced yield for making a definitive diagnosis from the biopsy sample. Another issue is that of false negative biopsy results, where a benign result may be obtained for a malignant thyroid. Lack of experience with ultrasound for some users can also result in prolonged and/or difficult-to-perform interventions, leading to patient trauma and frustration for the clinician.

SUMMARY

While existing ultrasound imaging has proved useful for clinical guidance and diagnosis, there remains a clinical need for improved systems and techniques for providing automated biopsy guidance tools. Embodiments of the present disclosure provide a deep learning framework to assist and guide a user in determining and performing a biopsy. The disclosed embodiments may identify one or more locations in a live ultrasound image that are suspicious of cancer and one or more locations to be excluded due to an expected non-diagnostic/benign result. The disclosed embodiments may display a cancer suspicion map overlaid on the live ultrasound image with a predicted probability of malignancy for each pixel, along with a corresponding confidence map for the prediction. The deep learning predictive network can also identify organs at risk (OARs) or critical structures in the live ultrasound image. The disclosed embodiments may determine one or more optimal biopsy paths in the live ultrasound image that can maximize yield and avoid critical structures. The disclosed embodiments can display the optimal biopsy paths via a contextual user interface, for example, providing a display of the needle paths with respect to the position of an ultrasound imaging probe in use and/or with respect to a target biopsy location. The disclosed embodiments may provide a user interface to guide a user in maneuvering an ultrasound imaging probe from a sub-optimal position to a position that can provide an optimal image for guiding a biopsy sample. The disclosed embodiments may provide warnings to a user when the user attempts to insert the needle in a trajectory that may endanger an OAR or one that might not reach the target.

In one embodiment, an ultrasound imaging system includes a communication interface in communication with an ultrasound imaging device and configured to receive a ultrasound image of a subject's anatomy; and a processor in communication with the communication interface and configured to: apply a predictive network to the ultrasound image to: identify a plurality of locations of potential malignancies in the subject's anatomy; and determine a plurality of malignancy likelihoods at the plurality of locations of potential malignancies; and output, to a display in communication with the processor, the plurality of locations of potential malignancies and the plurality of malignancy likelihoods for the plurality of locations of potential malignancies to guide a biopsy determination for the subject's anatomy.

In some embodiments, wherein the ultrasound image includes at least one of brightness-mode (B-mode) information, strain information, elasticity information, or tissue Doppler information. In some embodiments, wherein the processor is further configured to apply the predictive network to the ultrasound image to identify a critical region of the subject's anatomy to avoid for a biopsy; and determine a plurality of confidence levels for the plurality of malignancy likelihoods at the plurality of locations of potential malignancies. In some embodiments, wherein the processor is further configured to output, to the display, an overlay of indications of at least one of the plurality of locations of potential malignancies, the plurality of malignancy likelihoods, the plurality of confidence levels, or the critical region on the ultrasound image. In some embodiments, the system further comprises the display configured to display a first map including an overlay of indications of the plurality of locations of potential malignancies, the plurality of malignancy likelihoods, and the critical region on a first instance of the ultrasound image; and a second map including an overlay of indications of the plurality of confidence levels at the plurality of locations of potential malignancies on a second instance of the ultrasound image. In some embodiments, wherein the processor is further configured to determine a biopsy needle path for performing a biopsy on the subject's anatomy based on at least one of the plurality of locations of potential malignancies, the critical region, or a target biopsy location in the subject's anatomy. In some embodiments, wherein the processor is further configured to determine a target biopsy location for the subject's anatomy based on at least one of the plurality of malignancy likelihoods at the plurality of locations of potential malignancies or the plurality of confidence levels for the plurality of malignancy likelihoods, and wherein the biopsy needle path is further determined based on the determined target biopsy location. In some embodiments, the system further comprises a user interface in communication with the processor and configured to receive a selection of the target biopsy location. In some embodiments, wherein the processor is further configured to output, to the display, the determined biopsy needle path as an overlay on the ultrasound image. In some embodiments, wherein the processor is further configured to apply the predictive network to the ultrasound image to determine the biopsy needle path. In some embodiments, wherein the processor is further configured to determine that the critical region is along a trajectory path of a biopsy needle directed towards the subject's anatomy; and output, to the display, an indication of a potential collision between the biopsy needle and the critical region. In some embodiments, wherein the ultrasound image is received while the ultrasound imaging device is positioned at a first imaging position with respect to the subject's anatomy, and wherein the processor is further configured to apply the predictive network to the ultrasound image to determine a motion control configuration for repositioning the ultrasound imaging device from the first imaging position to a second imaging position for performing the biopsy; and output, to the display, a visual indicator for repositioning the ultrasound imaging device based on the motion control configuration. In some embodiments, wherein the predictive network is trained by providing a plurality of test ultrasound images of a test subject's anatomy, a biopsy location of a biopsy performed on test subject's anatomy, and a pathology result of the biopsy performed at the biopsy location; and assigning scores to pixels of the plurality of test ultrasound images based on the biopsy locations and the pathology result. In some embodiments, wherein the processor is further configured to update the predictive network based on at least one of a target biopsy location for a biopsy determined based on the plurality of locations of potential malignancies and the plurality of malignancy likelihoods; or a pathology result of the biopsy. In some embodiments, wherein the subject's anatomy includes at least a portion of a thyroid.

In one embodiment, a method of ultrasound imaging includes receiving, from an ultrasound imaging device, a ultrasound image of a subject's anatomy; applying a predictive network to the ultrasound image to identify a plurality of locations of potential malignancies in the subject's anatomy; and determine a plurality of malignancy likelihoods at the plurality of locations of potential malignancies; and displaying, by a display, the plurality of locations of potential malignancies and the plurality of malignancy likelihoods for the plurality of locations of potential malignancies to guide a biopsy determination for the subject's anatomy.

In some embodiments, wherein the applying the predictive network includes identifying a critical region of the subject's anatomy to avoid for a biopsy; and determining a plurality of confidence levels for the plurality of malignancy likelihoods at the plurality of locations of potential malignancies, and wherein the displaying includes displaying a first map including an overlay of indications of the plurality of locations of potential malignancies, the plurality of malignancy likelihoods, and the critical region on a first instance of the ultrasound image; and displaying a second map including an overlay of indications of the plurality of confidence levels on a second instance of the ultrasound image corresponding to the plurality of locations of potential malignancies. In some embodiments, the method further comprises determining a target biopsy location for performing a biopsy on the subject's anatomy based on at least one of the plurality of malignancy likelihoods at the plurality of locations of potential malignancies or the plurality of confidence levels for the plurality of malignancy likelihoods; determining a biopsy needle path for performing the biopsy based on at least one of the plurality of locations of potential malignancies, the critical region, or the target biopsy location of the subject's anatomy; and displaying, by the display, the determined biopsy needle path as an overlay on the first map. In some embodiments, the method further comprises determining that the critical region is along a trajectory path of a biopsy needle directed towards the subject's anatomy; and displaying, by the display, an indication of a potential collision between the biopsy needle and the critical region. In some embodiments, wherein the ultrasound image is received while the ultrasound imaging device is positioned at a first imaging position with respect to the subject's anatomy, and wherein the method further comprises applying the predictive network to the ultrasound image to determine a motion control configuration for repositioning the ultrasound imaging device from the first imaging position to a second imaging position for performing the biopsy; and displaying, by the display, a visual indicator for repositioning the ultrasound imaging device based on the motion control configuration.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
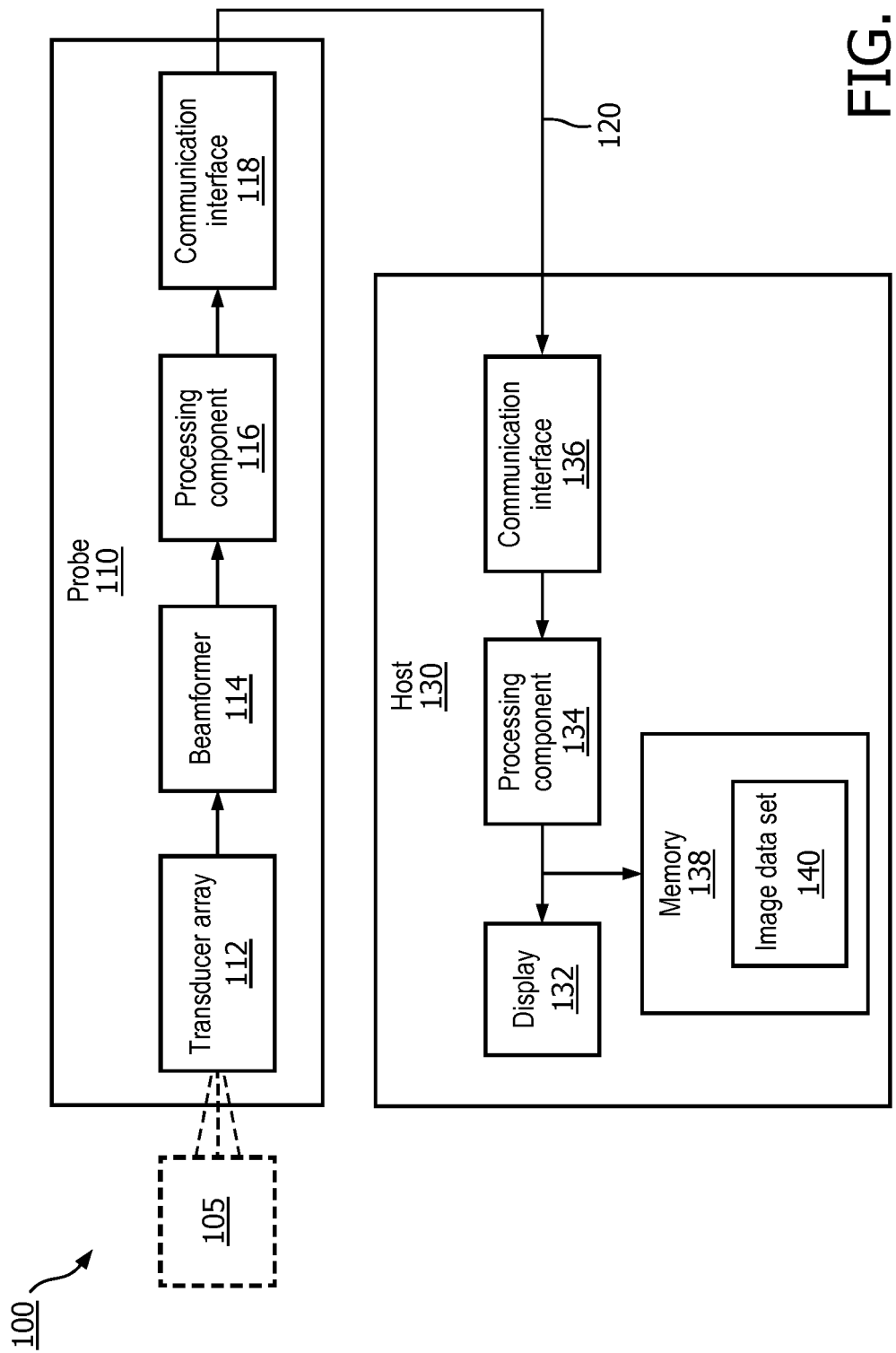
FIG. 1 is a schematic diagram of an ultrasound imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic diagram of an ultrasound imaging system 100, according to aspects of the present disclosure. The system 100 is used for scanning an area or volume of a patient's body. The system 100 includes an ultrasound imaging probe 110 in communication with a host 130 over a communication interface or link 120. The probe 110 includes a transducer array 112, a beamformer 114, a processing component 116, and a communication interface 118. The host 130 includes a display 132, a processing component 134, and a communication interface 136.

In an exemplary embodiment, the probe 110 is an external ultrasound imaging device including a housing configured for handheld operation by a user. The transducer array 112 can be configured to obtain ultrasound data while the user grasps the housing of the probe 110 such that the transducer array 112 is positioned adjacent to and/or in contact with a patient's skin. The probe 110 is configured to obtain ultrasound data of anatomy within the patient's body while the probe 110 is positioned outside of the patient's body.

The transducer array 112 emits ultrasound signals towards an anatomical object 105 and receives echo signals reflected from the object 105 back to the transducer array 112. The ultrasound transducer array 112 can include any suitable number of acoustic elements, including one or more acoustic elements and/or plurality of acoustic elements. In some instances, the transducer array 112 includes a single acoustic element. In some instances, the transducer array 112 may include an array of acoustic elements with any number of acoustic elements in any suitable configuration. For example, the transducer array 112 can include between 1 acoustic element and 1000 acoustic elements, including values such as 2 acoustic elements, 4 acoustic elements, 36 acoustic elements, 64 acoustic elements, 128 acoustic elements, 500 acoustic elements, 812 acoustic elements, and/or other values both larger and smaller. In some instances, the transducer array 112 may include an array of acoustic elements with any number of acoustic elements in any suitable configuration, such as a linear array, a planar array, a curved array, a curvilinear array, a circumferential array, an annular array, a phased array, a matrix array, a one-dimensional (1D) array, a 1.x dimensional array (e.g., a 1.5D array), or a two-dimensional (2D) array. The array of acoustic elements (e.g., one or more rows, one or more columns, and/or one or more orientations) that can be uniformly or independently controlled and activated. The transducer array 112 can be configured to obtain one-dimensional, two-dimensional, and/or three-dimensional images of patient anatomy. In some embodiments, the transducer array 112 may include a piezoelectric micromachined ultrasound transducer (PMUT), capacitive micromachined ultrasonic transducer (CMUT), single crystal, lead zirconate titanate (PZT), PZT composite, other suitable transducer types, and/or combinations thereof.

The beamformer 114 is coupled to the transducer array 112. The beamformer 114 controls the transducer array 112, for example, for transmission of the ultrasound signals and reception of the ultrasound echo signals. The beamformer 114 provides image signals to the processing component 116 based on the response or the received ultrasound echo signals. The beamformer 114 may include multiple stages of beamforming. The beamforming can reduce the number of signal lines for coupling to the processing component 116. In some embodiments, the transducer array 112 in combination with the beamformer 114 may be referred to as an ultrasound imaging component.

In some embodiments, the object 105 may include at least a portion of a patient's thyroid for biopsy. In other embodiments, the object 105 may include any anatomy (e.g., lung, blood vessel, heart, kidney, and/or liver) of a patient that is suitable for ultrasound imaging examination.

The processing component 116 is coupled to the beamformer 114. The processing component 116 may include a central processing unit (CPU), a digital signal processor (DSP), an application specific integrated circuit (ASIC), a controller, a field programmable gate array (FPGA) device, another hardware device, a firmware device, or any combination thereof configured to perform the operations described herein. The processing component 134 may also be implemented as a combination of computing devices, e.g., a combination of a DSP and a microprocessor, a plurality of microprocessors, one or more microprocessors in conjunction with a DSP core, or any other such configuration. The processing component 116 is configured to process the beamformed image signals. For example, the processing component 116 may perform filtering and/or quadrature demodulation to condition the image signals. The processing component 116 and/or 134 can be configured to control the array 112 to obtain ultrasound data associated with the object 105.

The communication interface 118 is coupled to the processing component 116. The communication interface 118 may include one or more transmitters, one or more receivers, one or more transceivers, and/or circuitry for transmitting and/or receiving communication signals. The communication interface 118 can include hardware components and/or software components implementing a particular communication protocol suitable for transporting signals over the communication link 120 to the host 130. The communication interface 118 can be referred to as a communication device or a communication interface module.

The communication link 120 may be any suitable communication link. For example, the communication link 120 may be a wired link, such as a universal serial bus (USB) link or an Ethernet link. Alternatively, the communication link 120 nay be a wireless link, such as an ultra-wideband (UWB) link, an Institute of Electrical and Electronics Engineers (IEEE) 802.11 WiFi link, or a Bluetooth link.

At the host 130, the communication interface 136 may receive the image signals. The communication interface 136 may be substantially similar to the communication interface 118. The host 130 may be any suitable computing and display device, such as a workstation, a personal computer (PC), a laptop, a tablet, or a mobile phone.

The processing component 134 is coupled to the communication interface 136. The processing component 134 may be implemented as a combination of software components and hardware components. The processing component 134 may include a central processing unit (CPU), a graphics processing unit (GPU), a digital signal processor (DSP), an application-specific integrated circuit (ASIC), a controller, a FPGA device, another hardware device, a firmware device, or any combination thereof configured to perform the operations described herein. The processing component 134 may also be implemented as a combination of computing devices, e.g., a combination of a DSP and a microprocessor, a plurality of microprocessors, one or more microprocessors in conjunction with a DSP core, or any other such configuration. The processing component 134 can be configured to generate image data from the image signals received from the probe 110. The processing component 134 can apply advanced signal processing and/or image processing techniques to the image signals. In some embodiments, the processing component 134 can form three-dimensional (3D) volume image from the image data. In some embodiments, the processing component 134 can perform real-time processing on the image data to provide a streaming video of ultrasound images of the object 105.

In some embodiments, the processing component 134 can perform image analysis on the image data or image frames for biopsy determination. For example, the processing component 134 can receive ultrasound images of the object 105 including tissues of a patient. The processing component 134 can apply deep-learning-based techniques to determine locations of potential malignancies or abnormalities at the patient's tissues, determine whether a biopsy is needed, identify a target biopsy location, and/or suggest potential needle paths to reach the target location avoiding critical organs or areas of the tissues. The processing component 134 can apply deep-learning-based techniques to determine whether an imaging plane can provide an optimal view of the target biopsy location and how to guide a user in maneuvering the probe 110 to an optimal view for guiding the biopsy. The processing component 134 can monitor an insertion or entry point of a biopsy needle selected by a clinician, determine trajectories of the biopsy needle that can collide with reach a critical area of the tissues, and/or generate a warning to the clinician when a collision between a trajectory of the biopsy needle and a critical area may occur. Mechanisms for predicting and guiding a biopsy are described in greater detail herein.

The display 132 is coupled to the processing component 134. The display 132 may be a monitor or any suitable display. The display 132 is configured to display ultrasound images, image videos, and/or information associated with tissue locations of potential malignancies, target biopsy locations, suggested biopsy needle paths, instructions to move the probe 110 to an optimal imaging view for a biopsy, and/or warnings regarding a biopsy generated by the processing component 134, as described in greater detail herein.

The system 100 can be configured for use in various stages of ultrasound imaging-based biopsy prediction and guidance procedures. In an embodiment, the system 100 may be used for collecting ultrasound images to form training data set for deep learning network training. For example, the host 130 may include a memory 138, which may be any suitable storage device, such as a cache memory (e.g., a cache memory of the processing component 134), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, solid state drives, other forms of volatile and non-volatile memory, or a combination of different types of memory. The memory 138 can be configured to store an image data set 140 for deep learning-based training.

In some embodiments, the system 100 may be used for training deep learning networks for biopsy prediction and guidance. For example, a deep learning network may be trained using ultrasound images of tissues including areas that are potentially malignant, target locations applied to the tissues for biopsies, and/or corresponding pathology results obtained from the biopsies. The deep learning network may be trained to identify tissue locations that are potentially malignant, identify critical areas (e.g., organ-at-risk (OAR)) to avoid for a biopsy, and/or determine the probabilities of malignancies and associated confidence levels at the identified locations. The deep learning network may be trained to determine a biopsy target location based on identified tissue locations of potential malignancies and/or determine one or more biopsy needle paths to reach a target avoiding critical areas. The deep learning network may be trained to determine movements for maneuvering the probe 110 to an imaging plane suitable for guiding a biopsy.

In some embodiments, the system 100 may be used in a clinical setting for live biopsy procedures, where the trained deep learning networks may be applied to determine whether a biopsy is needed, identify tissue locations of potential malignancies, determine a target biopsy location, and/or suggest one or more needle paths for biopsy avoiding critical areas. Mechanisms for automatically and systematically for predicting and guiding a biopsy procedure based on deep learning-based techniques are described in greater detail herein.

Figure 2:
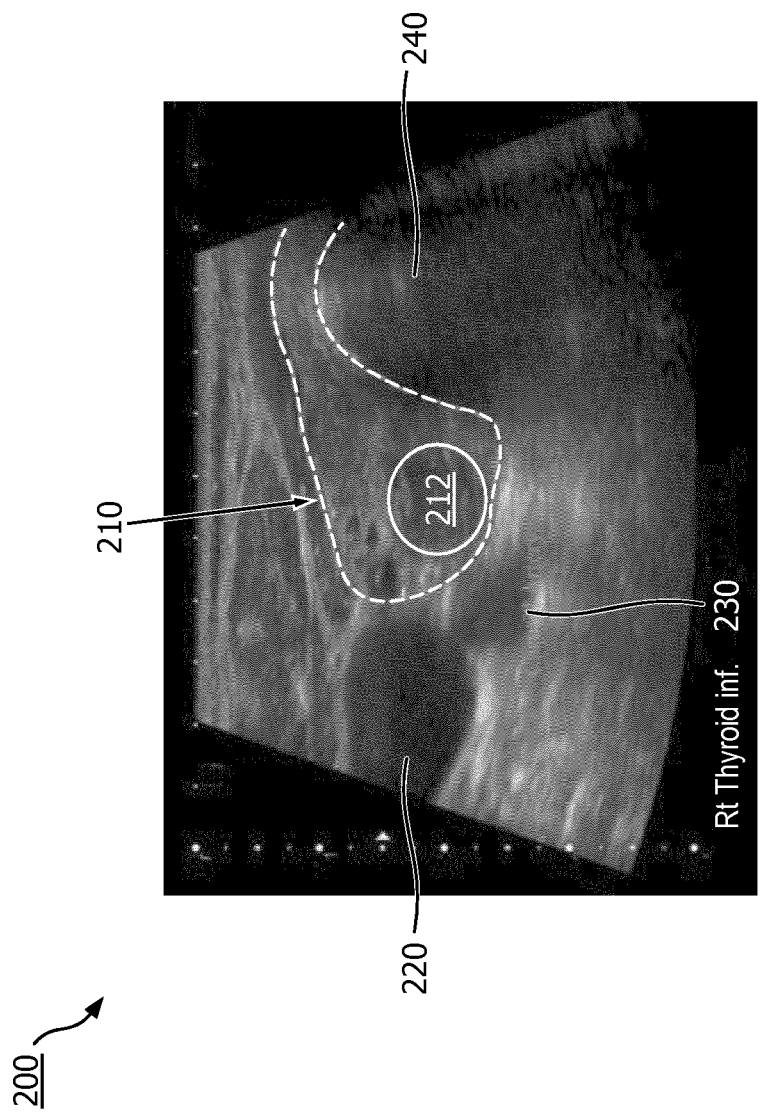
FIG. 2 is an ultrasound image of a patient's thyroid and surrounding areas, according to aspects of the present disclosure.

FIG. 2 is an ultrasound image 200 of a patient's thyroid 210 and surrounding areas, according to aspects of the present disclosure. The image 200 may be captured using a system similar to the system 100. The image 200 shows a nodule 212 in the patient's thyroid and structures and/or tissues close to the patient's thyroid. The nodule 212 can be malignant or benign. A biopsy may need to be performed on the nodule 212 to determine whether the nodule 212 is malignant or benign. Some structures and/or tissues are critical structures or organ-at-risk (OAR) where a biopsy needle path needs to avoid. As shown, an internal jugular vein 220, a carotid artery 230, and a trachea 240 are in proximity to the thyroid 210. The internal jugular vein 220, the carotid artery 230, and the trachea 240 are critical structures. Thus, when performing a biopsy on the nodule 212, the internal jugular vein 220, the carotid artery 230, and the trachea 240 cannot be along the biopsy needle path.

FIGS. 3-12 collectively illustrate the use of deep learning-based techniques in a biopsy work flow to automatically and systematically to predict a biopsy location, a biopsy needle path, and guide a biopsy procedure.

Figure 3:
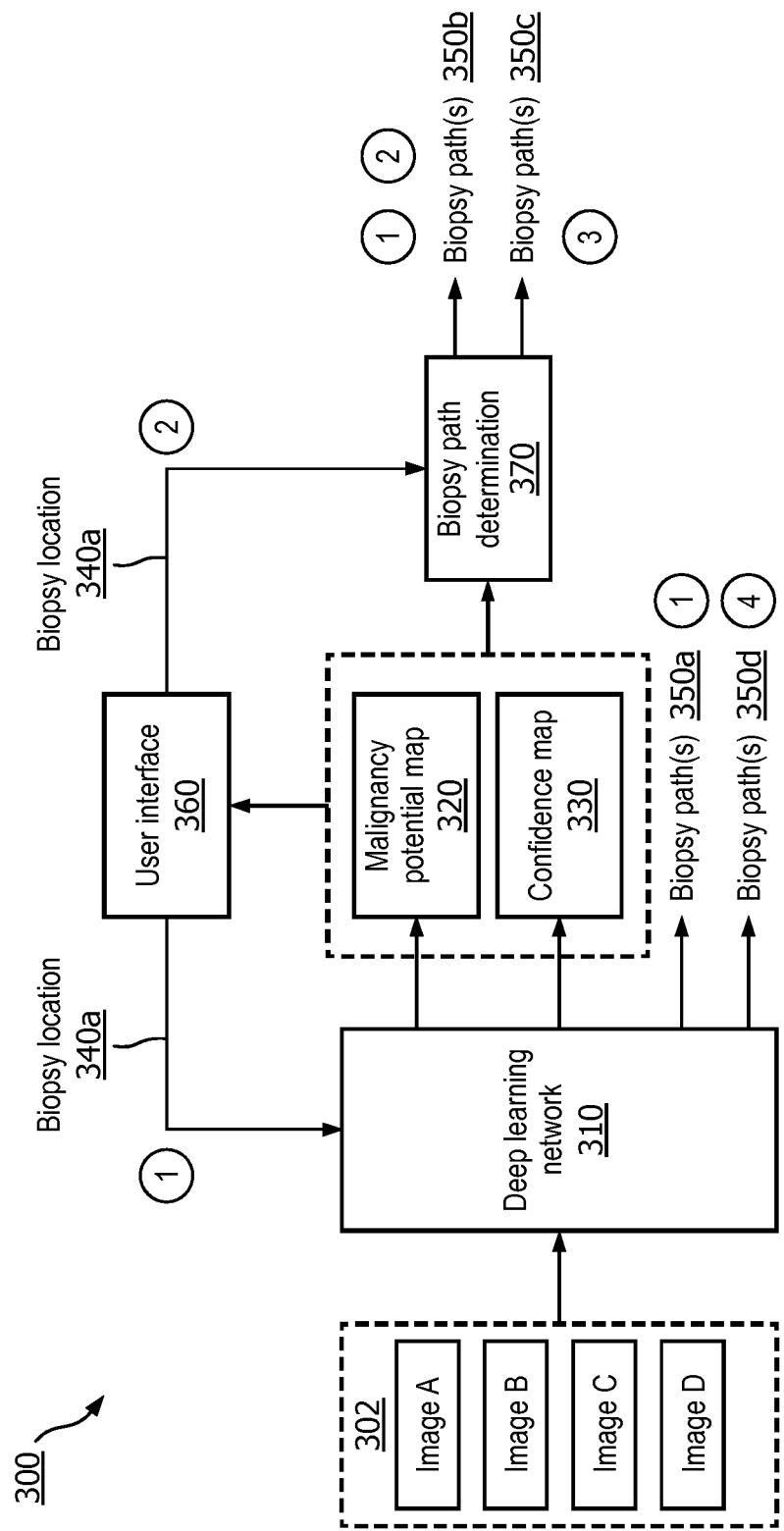
FIG. 3 is a schematic diagram illustrating an automated pixel-level ultrasound image annotation and needle path prediction scheme, according to aspects of the present disclosure.

FIG. 3 is a schematic diagram illustrating an automated pixel-level ultrasound image annotation and needle path prediction scheme 300, according to aspects of the present disclosure. The scheme 300 is implemented by the system 100. The scheme 300 can provide biopsy guidance to a clinician preparing for a biopsy examination (e.g., prior to a needle insertion). The clinician may capture one or more images 302 of a patient's tissues (e.g., the object 105) under an examination for a potential biopsy using the probe 110. In an embodiment, the tissues can include at least a portion of the patient's thyroid (e.g., the thyroid 210) and the biopsy can be a thyroid biopsy to determine whether the thyroid includes abnormal cells (e.g., malignancies). The images 302 can be captured using B-mode and optionally in combination with various ultrasound imaging modalities. The images 302 may provide various imaging information including B-mode imaging information, strain imaging information, modulus imaging information, Doppler imaging information (e.g., power Doppler, color flow, and spectral Doppler), and tissue Doppler imaging (TDI) information and/or any suitable imaging information that can facilitate the analysis of imaging data for locating potential malignancies and predicting and guiding a biopsy. For purposes of simplicity for illustration and discussions, FIG. 3 illustrates four images 302. However, a clinician may capture any suitable number of images 302 (e.g., 5, 6 or more) in any suitable number of ultrasound imaging modalities (e.g., about 5, 6 or more) for a biopsy procedure. As an example, the images 302 may include an image A captured using B-mode, an image B captured using a strain imaging mode, an image C 302 captured using a Shear/Young's modulus imaging mode, and an image D 302 in a TDI mode.

In an embodiment, the images B, C, and D 302 of the various modalities (e.g., strain, modulus, Doppler, and TDI) can be registered to the underlying B-mode image A 302. The system 100 can be configured to capture the images 302 in the different modalities by interleaving one or more of the strain, modules, Doppler, and TDI modalities with B-mode imaging. The system 100 can display any of the images 302 on the display 132. In some embodiments, the clinician may select the B-mode image A 302 for display on the display 132. The B-mode image A 302 can be similar to the image 200.

The images 302 are sent to the processing component 134 at the host 130. The processing component 134 receives the images 302 and applies a deep learning network 310 to the received images 302. The deep learning network 310 is trained to predict a probability of malignancies for each pixel on an input image (e.g., the images 302), as described in greater detail herein. The deep learning network 310 may identify tissue locations that are suspicious of malignant from the patient's tissues captured by the images 302. The deep learning network 310 may identify critical areas or OARs (e.g., the internal jugular vein 220, the carotid artery 230, and the trachea 240) in the patient's tissues that a biopsy needle path needs to avoid. The deep learning network 310 may determine malignancy likelihoods at the identified potential malignant tissue locations. The deep learning network 310 may determine confidence levels for the prediction or determination of the malignancy likelihoods at the identified potential malignant tissue locations. In some embodiments, the deep learning network 310 can identify tissue locations that are non-diagnostic and/or benign from the patient's tissues captured by the images 302. The non-diagnostic and/or benign tissue locations can be excluded from a target biopsy location selection. The architecture of the deep learning network 310 and the training of the deep learning network 310 are described in greater detail herein. In some embodiments, the critical areas or OARs may be computed using any suitable OAR segmentation methods, such as thresholding, active contours, and/or machine learning based segmentation methods instead of using the deep learning network 310.

Figure 4:
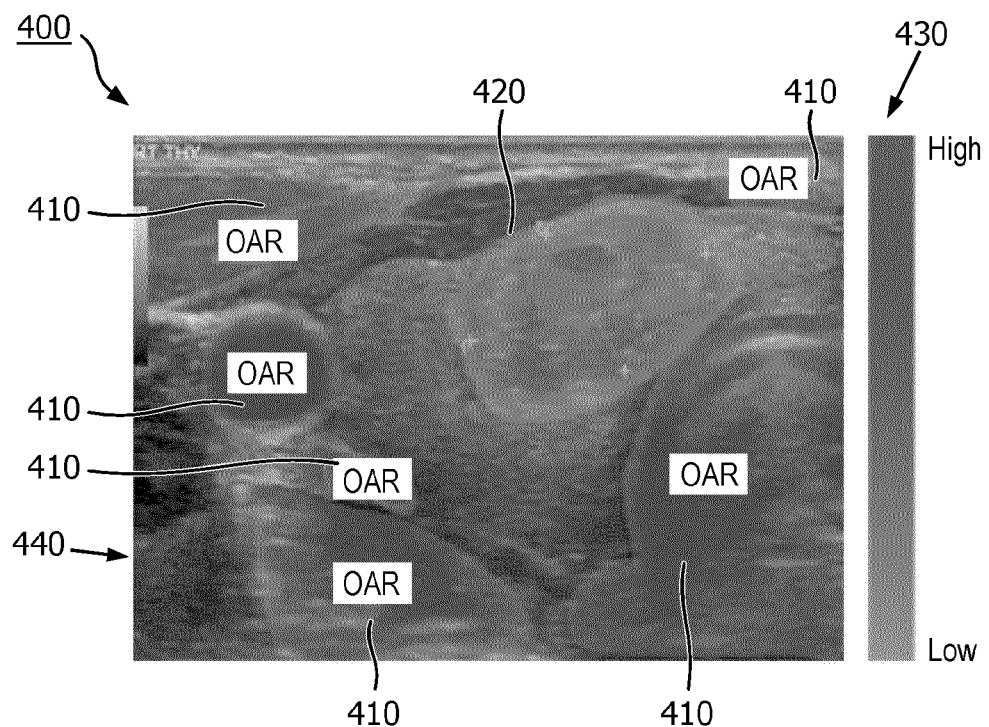
FIG. 4 is a graphical display of a malignancy potential map for an ultrasound image, according to aspects of the present disclosure.
Figure 5:
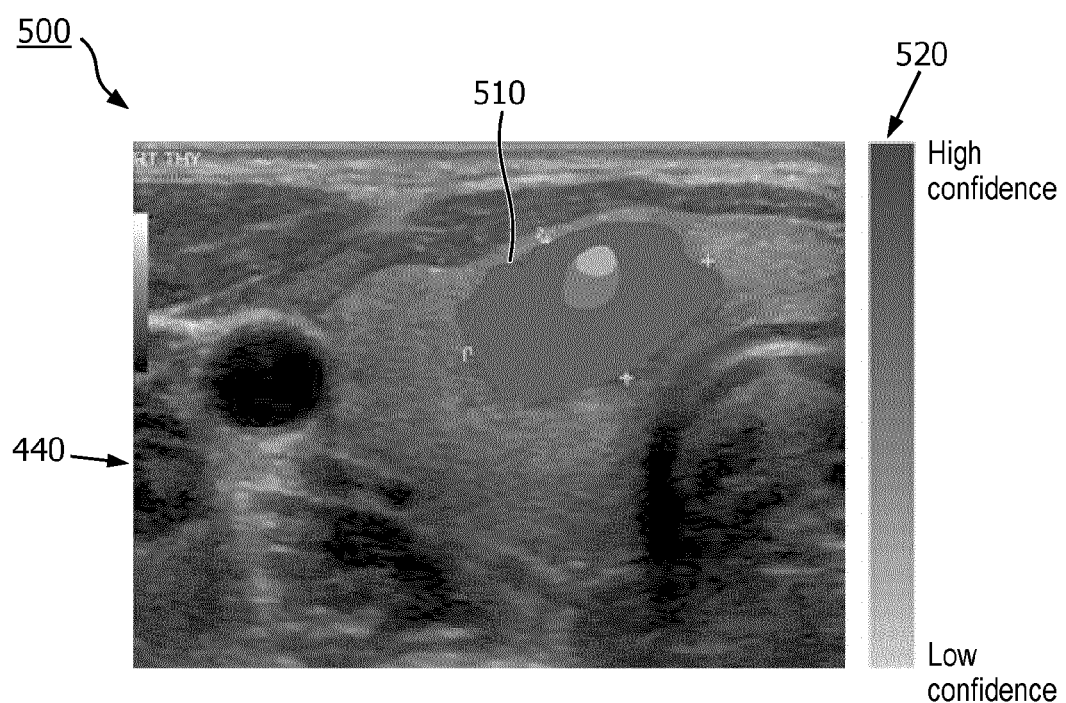
FIG. 5 is a graphical display of a malignancy likelihood confidence map for an ultrasound image, according to aspects of the present disclosure.

The deep learning network 310 outputs a malignancy potential map 320 and a confidence map 330 based on the identified potential malignant tissue locations, the identified critical areas, the determined malignancy likelihoods and corresponding confidence levels. The malignancy potential map 320 can be referred to as a suspicion map. Examples of the malignancy potential map 320 and the confidence map 330 are shown in FIGS. 4 and 5 described below. The processing component 134 can output the malignancy potential map 320 and the confidence map 330 to a user interface 360 (e.g., the display 132).

FIG. 4 is a graphical display of a malignancy potential map 400 for an underlying ultrasound image 440, according to aspects of the present disclosure. The malignancy potential map 400 may correspond to the malignancy potential map 320 of FIG. 3. The image 440 may correspond to the B-mode image A 302 of FIG. 3. The malignancy potential map 400 can be displayed on the display 132 or the user interface 360. The malignancy potential map 400 includes an overlay of OARs 410 and potential malignant tissue locations 420 and corresponding malignancy likelihoods on the image 440. The potential malignant tissue locations 420 are shown as closed surface shapes. The OARs 410 are shown as closed surface shapes and opened surface shapes. The malignancy map 400 can include text annotations for the OARs 410 as shown. The gaps between the OARs 410 and the potential malignant tissue locations 420 represent no specific information related to malignancies and/or biopsies is obtained from the prediction. The potential malignant tissue locations 420 can be color-coded according to the malignancy likelihoods. For example, a color scheme 430 can use a first color (e.g., green) to represent a low malignancy likelihood and gradually transition to a second color (e.g., red) to represent a high malignancy likelihood.

FIG. 5 is a graphical display of a malignancy likelihood confidence map 500 for the underlying ultrasound image 440, according to aspects of the present disclosure. The confidence map 500 may correspond to the confidence map 330 of FIG. 3. The confidence map 500 can be displayed on the display 132 or the user interface 360. The confidence map 500 includes an overlay of confidence levels 510 (shown as a closed surface shape) corresponding to the malignancy likelihoods at the potential malignant locations 420 of FIG. 4 on the image 440. Similar to the malignancy potential map 400, the confidence levels 510 can be color-coded. For example, a color scheme 520 can use a first color (e.g., light blue) to represent a low confidence level and gradually transition to a second color (e.g., dark blue) red to represent a high confidence levels.

The confidence map 500 may have a one-to-one correspondence with the malignancy potential map 400 (e.g., at pixel-level). The confidence map 500 and the malignancy potential map 400 can be displayed simultaneously on the display 132. While FIGS. 4 and 5 illustrate the malignancy potential map 400 and the confidence map 500 overlaid on the B-mode image 440, in some other embodiments, the malignancy potential map 400 and the confidence map 500 can be overlaid on an ultrasound image of another ultrasound imaging modality (e.g., TDI, strain, or modulus).

As can be observed from FIGS. 4 and 5, areas that have low likelihoods of malignancy (e.g., low suspicion for cancer) can be predicted with a high confidence levels, areas that have high likelihoods of malignancy (e.g., high suspicion for cancer) can be predicted with a low confidence levels, and areas that has intermediate likelihoods of malignancy (e.g., intermediate suspicion of cancer) can be predicted with a reasonable confidence.

Returning to FIG. 3, after determining the malignancy potential map 320 and the corresponding confidence map 330, a target biopsy location 340 and one or more biopsy needle paths 350 can be identified from the malignancy potential map 320 and the corresponding confidence map 330 using various mechanisms.

In a first example as marked by a circle labeled 1 in FIG. 3, the clinician may select the target biopsy location 340 based on the malignancy potential map 320 and the corresponding confidence map 330. For example, the clinician may select a target biopsy location 340a from a region of the tissues with an intermediate malignancy likelihood as the region with the intermediate malignancy likelihood may most likely provide a sufficient sample yield for pathology testing. The clinician may input the selection of the target biopsy location 340a via the user interface 360. The user-selected target biopsy location 340a can be input into the deep learning network 310. The deep learning network 310 can predict one or more biopsy needle paths $350a_{(1)}$ based the user-selected target biopsy location 340a and the identified critical areas (e.g., avoiding the OARs 410). The training of the deep learning network 310 to identify an optimal biopsy needle path to reach a biopsy target is as described in greater detail herein.

In a second example as marked by a circle labeled 2 in FIG. 3, the user-selected target biopsy location 340a can be input into a biopsy path determination unit 370. The biopsy path determination unit 370 can compute one or more biopsy needle paths 350b that can safely reach the identified target biopsy location 340 without intersecting any of the critical areas (e.g., the OARs 410). The biopsy path determination unit 370 can determine a trajectory for a needle path 350b based on certain constraints, for example, using image analysis algorithms and numerical optimization algorithms.

In a third example as marked by a circle labeled 3 in FIG. 3, the biopsy path determination unit 370 can determine a target biopsy location based on a weighted combination of the malignancy likelihoods in the malignancy potential map 320 and corresponding confidence levels in the confidence map 330. The biopsy path determination unit 370 can determine one or more biopsy needle paths 350c to reach the determined biopsy location based on trajectory computations.

In a fourth example as marked by a circle labeled 4 in FIG. 3, the deep learning network 310 can be trained to predict a target biopsy location and one or more biopsy needle paths 350d to reach the predicted biopsy target location based on the identified potential malignant tissue locations 420, the identified critical areas or OARs 410, and the determined malignancy likelihoods and corresponding confidence levels. For example, the deep learning network 310 can be trained to select a biopsy needle path 350d that can maximize yield and avoid intersecting any critical structures (e.g., the OARs 410). In other words, the deep learning network 310 can automatically suggest one or more biopsy needle paths 350d from one or more of the images 302.

In general, the malignancy potential map 320 and the confidence map 330 can assist a clinician in selecting a target biopsy location 340 and/or a biopsy needle path 350. The clinician may be provided with the options to use any suitable combinations of user-defined selection, deep learning-based predictions (e.g., by the deep learning network 310), and numerical computations (e.g., by the biopsy path determination unit 370).

Figure 6:
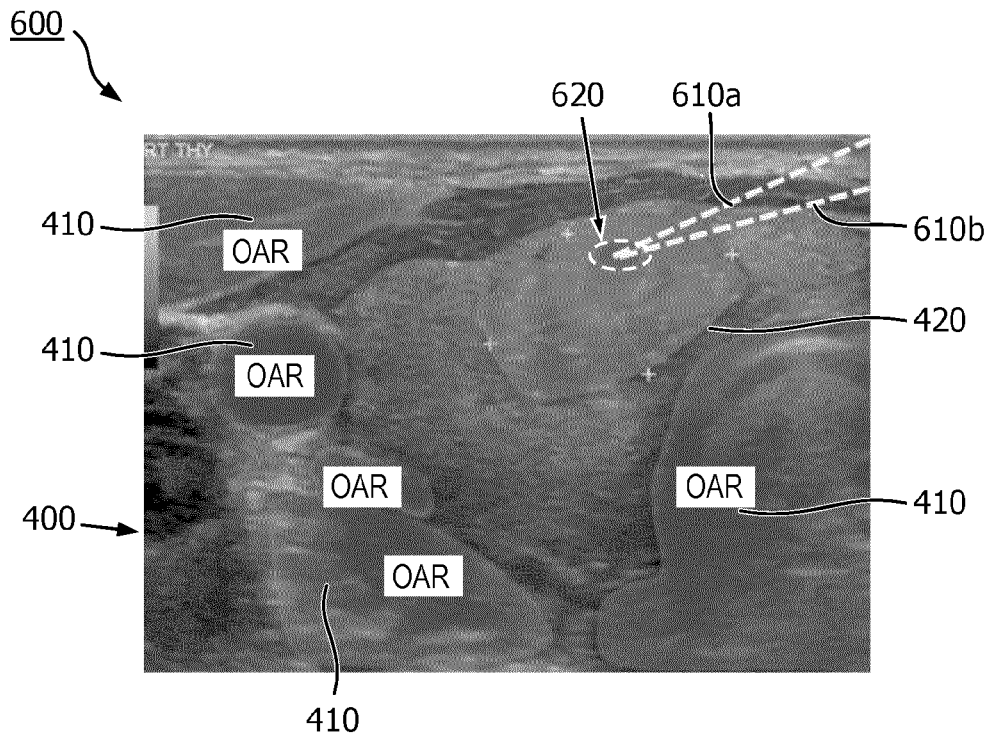
FIG. 6 is a graphical display of a malignancy potential map with visual indicators for biopsy needle paths, according to aspects of the present disclosure.

The processing component 134 can output the determined or suggested biopsy needle paths 350 to the display 132 as shown in FIG. 6 described below.

FIG. 6 is a graphical display of a malignancy potential map 600 with visual indicators for biopsy needle paths 610, according to aspects of the present disclosure. The malignancy potential map 600 may correspond to the malignancy potential map 400. The biopsy needle paths 610 are shown to reach a biopsy target 620 (as shown by the dotted oval). The biopsy target 620 and the biopsy needle paths 610 may correspond to the biopsy needle paths 350 and the biopsy target 620 may correspond to the target biopsy location 340 and the biopsy needle paths 350, respectively. While FIG. 6 is illustrated with two needle paths 610a and 610b, in some embodiments, any suitable number of need paths 610 (e.g., about 1, 3 or more) can be overlaid on the malignancy potential map 600.

Figure 7:
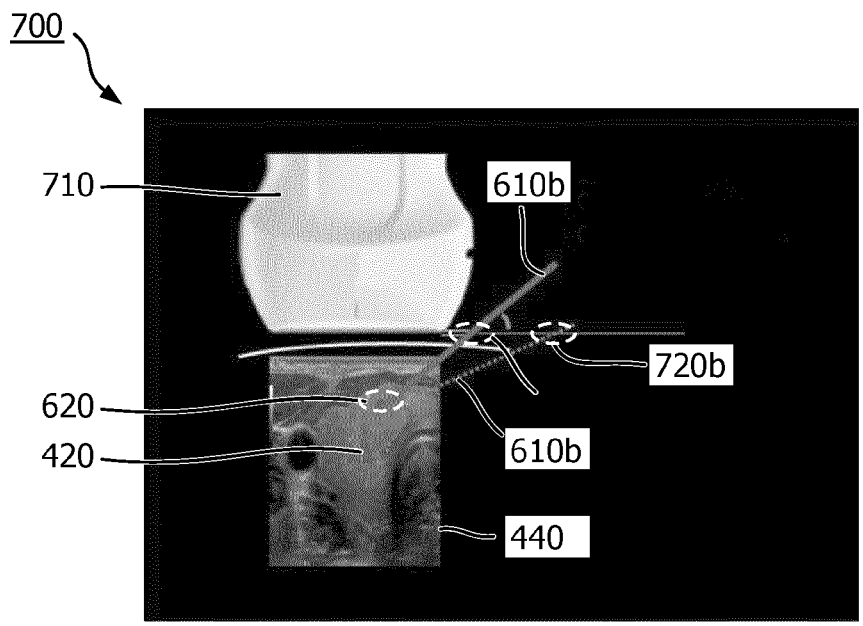
FIG. 7 is a graphical display of a context display including proposed biopsy needle paths in relation to an ultrasound probe and needle entry points, according to aspects of the present disclosure.

In some embodiments, the scheme 300 may also display the proposed needle paths 350 in relation to a needle entry point with respect to the patient's skin and/or the probe 110 in use to provide a more contextual visualization of the needle paths 350 for the user as shown in FIG. 7 described below.

FIG. 7 is a graphical display 700 of a contextual display including the proposed biopsy needle paths 610 in relation to an ultrasound probe 710 and needle entry points 720, according to aspects of the present disclosure. The display 700 may correspond to a display view on the display 132. The probe 710 may correspond to the probe 110. The biopsy needle paths 610 are overlaid on the B-mode image 440 along with the potential malignant tissue locations 420 and extend beyond the image 440. The needle entry points 720a and 720b may correspond to the skin entry points to access the needle paths 610a and 610b, respectively. For example, the needle path 610a may require a needle insertion at an angle of about 30 degrees to the patient's skin at the needle entry point 720a, while the needle path 610b may require a needle insertion at an angle of about 15 degrees to the patient's skin at the needle entry point 720b.

In some embodiments, the scheme 300 may consider additional factors when determining the biopsy needle paths 350. The additional factors may include whether the clinician is left-handed or right-handed, the position of the clinician with respect to the patient under examination, and/or the position of the nodule (e.g., the nodule 212) for biopsy with respect to the probe 110, for example, whether the probe 110 is towards the left or the right of the nodule.

Figure 8:
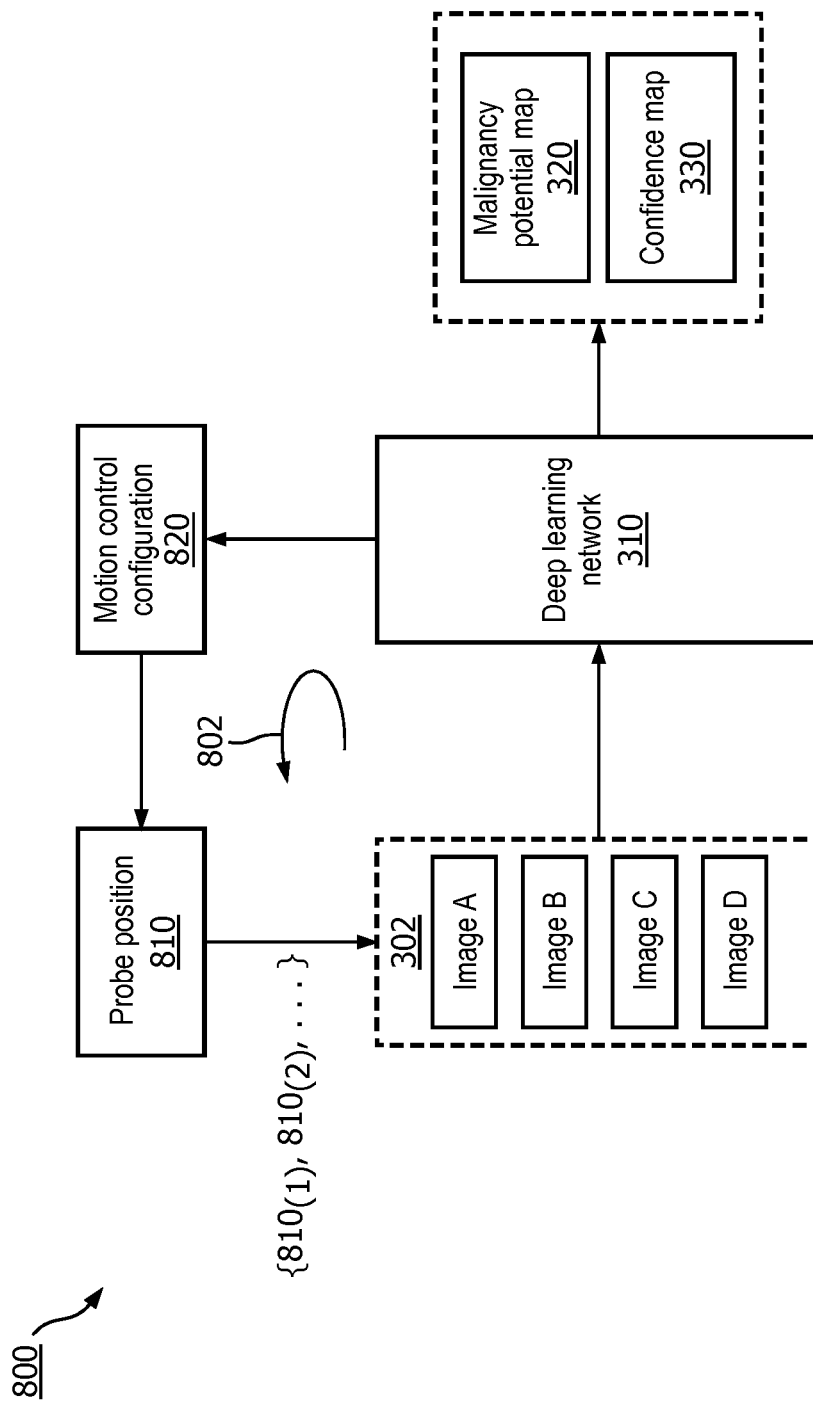
FIG. 8 is a schematic diagram illustrating an automated ultrasound probe position guidance scheme, according to aspects of the present disclosure.

FIG. 8 is a schematic diagram illustrating an automated ultrasound probe position guidance scheme 800, according to aspects of the present disclosure. The scheme 800 is implemented by the system 100. The scheme 800 is similar to the scheme 300, but may additionally provide ultrasound probe position guidance to a clinician preparing for a biopsy examination (e.g., prior to a needle insertion). In the scheme 800, a clinician may select an initial probe position $810_{(1)}$ for a probe (e.g., the probe 110) to capture images 302. The processing component 134 may determine that the probe position $810_{(1)}$ may provide a sub-optimal image plane for guiding a biopsy, for example, due to a biopsy target (e.g., the nodule 212) not being adequately present in the image plane and/or the position of one or more OARs (e.g., the internal jugular vein 220, the carotid artery 230, the trachea 240, and OARs 410) may not allow a needle to reach the target easily and/or safely without damaging the OARs.

Upon detecting a sub-optimal image plane, the processing component 134 can apply the deep learning network 310 to determine a motion control configuration 820 for maneuvering the probe to reach an optimal image plane for performing the biopsy. The motion control configuration 820 may include movement vectors for translating and/or rotating the probe from the initial position $810_{(1)}$ with respect to the patient to a next position $810_{(2)}$. The deep learning network 310 can learn the locations of the OARs with respect to one or more thyroid lobes during training of the deep learning network 310. The criteria for optimality (e.g., to reach an optimal imaging plane) can include the ability to reach the target biopsy location and maintaining a certain distance from all OARs. The processing component 134 can output instructions with visual indicators to the display 132 to provide feedbacks and/or suggestions to the clinician on how to manipulate the probe position in real-time as shown in FIG. 9 described below.

In some instances, the process of providing movement instructions (e.g., the motion control configuration 820) and maneuvering the probe can include multiple iterations. For example, the clinician may move the probe from a first position to a second position according to the instructions provided by the deep learning network 310. After the clinician moved the probe to the second position, the clinician may capture another set of images 302 and the deep learning network 310 may attempt to locate a biopsy target and a needle path from the newly captured images 302. When the newly captured images 302 cannot provide an optimal view for guiding the biopsy (e.g., based on the malignancy potential map 320 and the confidence map 330 output by the deep learning network 310), the process of determining a motion control configuration 820 can be repeated as shown by the arrow 802.

Figure 9:
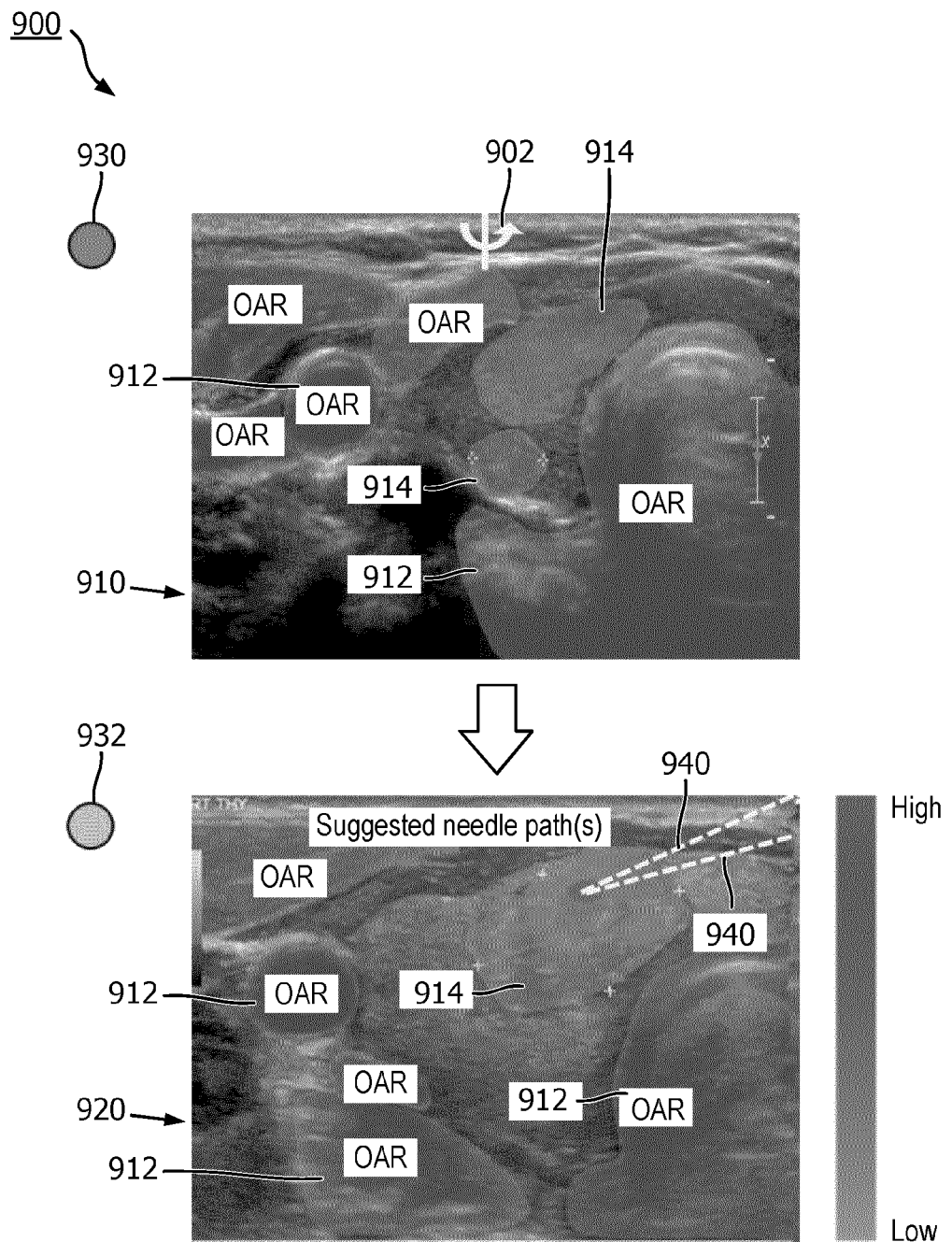
FIG. 9 is a graphical display of a user interface for guiding probe positioning, according to aspects of the present disclosure.

FIG. 9 is a graphical display for a user interface 900 for guiding probe positioning, according to aspects of the present disclosure. The user interface 900 can be displayed on the display 132 or the user interface 360. The user interface 900 includes a first image view 910 of a malignancy potential map (e.g., the malignancy potential maps 320 and 400) when a probe (e.g., the probe 110) is positioned at an initial imaging position (e.g., the probe position $810_{(1)}$). The first image view 910 may be sub-optimal due to the proximity of OARs 912 (e.g., the OARs 410) to potential malignant tissue locations 914 (e.g., the potential malignant tissue locations 420). The potential malignant tissue locations 914 are shown as a closed surface shape. The OARs 912 are shown as closed surface shapes and opened surface shapes.

The user interface 900 may include a suggestion to rotate the probe about its main handle axis as shown by the visual indicator 902. The clinician may follow the visual indicator 902 to rotate the probe (e.g., from the probe position $810_{(1)}$ to the probe position $810_{(2)}$). After the clinician rotates the probe, one or more images (e.g., the images 302) may be captured. The deep learning network 310 can be applied to generate another malignancy potential map as shown in the second image view 920, where.

In some embodiments, the user interface 900 can indicate sub-optimality by including a red dot 930 alongside the first sub-optimal image view 910 and a green dot 932 alongside the second sub-optimal image view 920. In some other instances, the user interface 900 may indicate the sub-optimality and/or the optimality of an image view using visual indicators of any suitable shapes and/or colours. After obtaining the second optimal image view 920, the user interface 900 can show proposed needle paths 940 (e.g., the biopsy needle paths 350, 610, and 940) in the second optimal image view 920.

Figure 10:
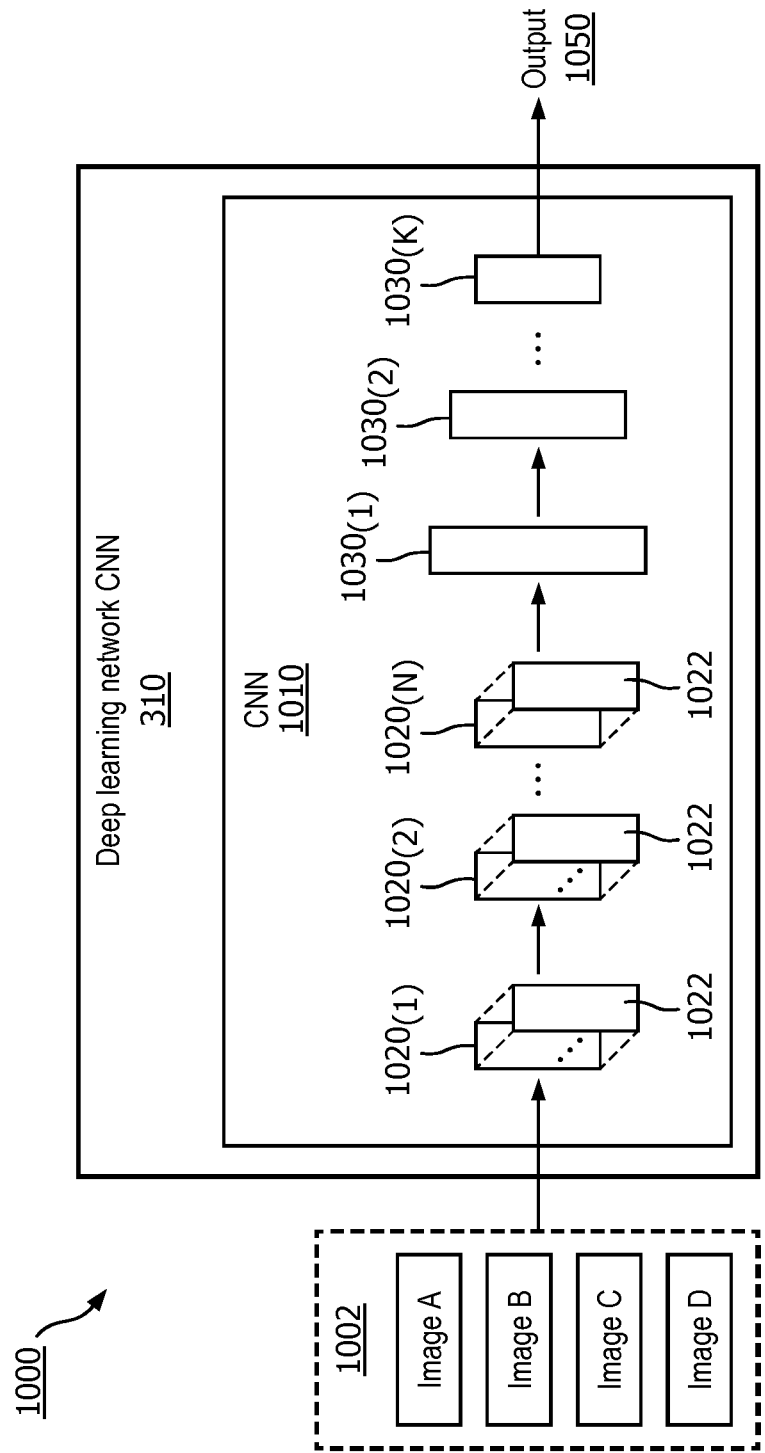
FIG. 10 is a schematic diagram illustrating a configuration of a deep learning network, according to aspects of the present disclosure.

FIG. 10 is a schematic diagram illustrating a configuration 1000 of the deep learning network 310, according to aspects of the present disclosure. The deep learning network 310 may include one or more convolutional neural networks (CNNs) 1010. The CNN 1010 may operate on one or more ultrasound images 1002 similar to the images 302. For example, the images 1002 may include an image A captured using B-mode and a combination of one or more of an image B captured using a strain imaging mode, an image C 302 captured using a Shear/Young's modulus imaging mode, and an image D 302 in a TDI mode.

The CNN 1010 may include a set of N convolutional layers 1020 followed by a set of K fully connected layers 1030, where N and K may be any positive integers. The values N and K may vary depending on the embodiments. In some instances, the values N and K may be dependent on the size of the training and/or validation data sets (e.g., the image data set 140). Each convolutional layer 1020 may include a set of filters 1022 configured to extract features from input images. While not shown in FIG. 10, in some embodiments, the convolutional layers 1020 may be interleaved with spatial pooling layers, each including a set of downsampling operations that may reduce the dimensionality of the extracted imaging features. In addition, each convolutional layer 512 may a include non-linearity function (e.g., including rectified non-linear (ReLU) operations) configured to extract rectified feature maps. Further, each convolutional layer 1020 may include a batch normalization function to speed up the training of the CNN 1010. The fully connected layers 1030 may be non-linear and may gradually shrink the high-dimensional output of the last convolutional layer $1020_{(N)}$ to produce an output 1050.

In an embodiment, the CNN 1010 is trained to predict a probability of malignancies for each pixel on an input image (e.g., the images 302 and 1002). In an embodiment, the CNN 1010 is trained to predict a biopsy target (e.g., the target biopsy locations 340 and the biopsy target 620) from an input image and/or a biopsy needle path (e.g., the biopsy needle paths 350, 610, and 940) to reach the biopsy target from the input image. In an embodiment, the CNN 1010 is trained to predict a motion control configuration (e.g., the motion control configuration 820) for moving a probe (e.g., the probe 110) from a current position to an optimal imaging position for guiding a biopsy given an input image captured by the probe while the probe is at the current position. The training of the CNN 1010 is described in greater detail herein.

While the CNN 1010 is illustrated as a fully convolutional neural network (FCN), in some embodiments, the CNN 1010 can be configured as an encoder-decoder type network (e.g., a U-net architecture) or any other suitable learning-based predictive network to achieve similar functionalities.

Figure 11:
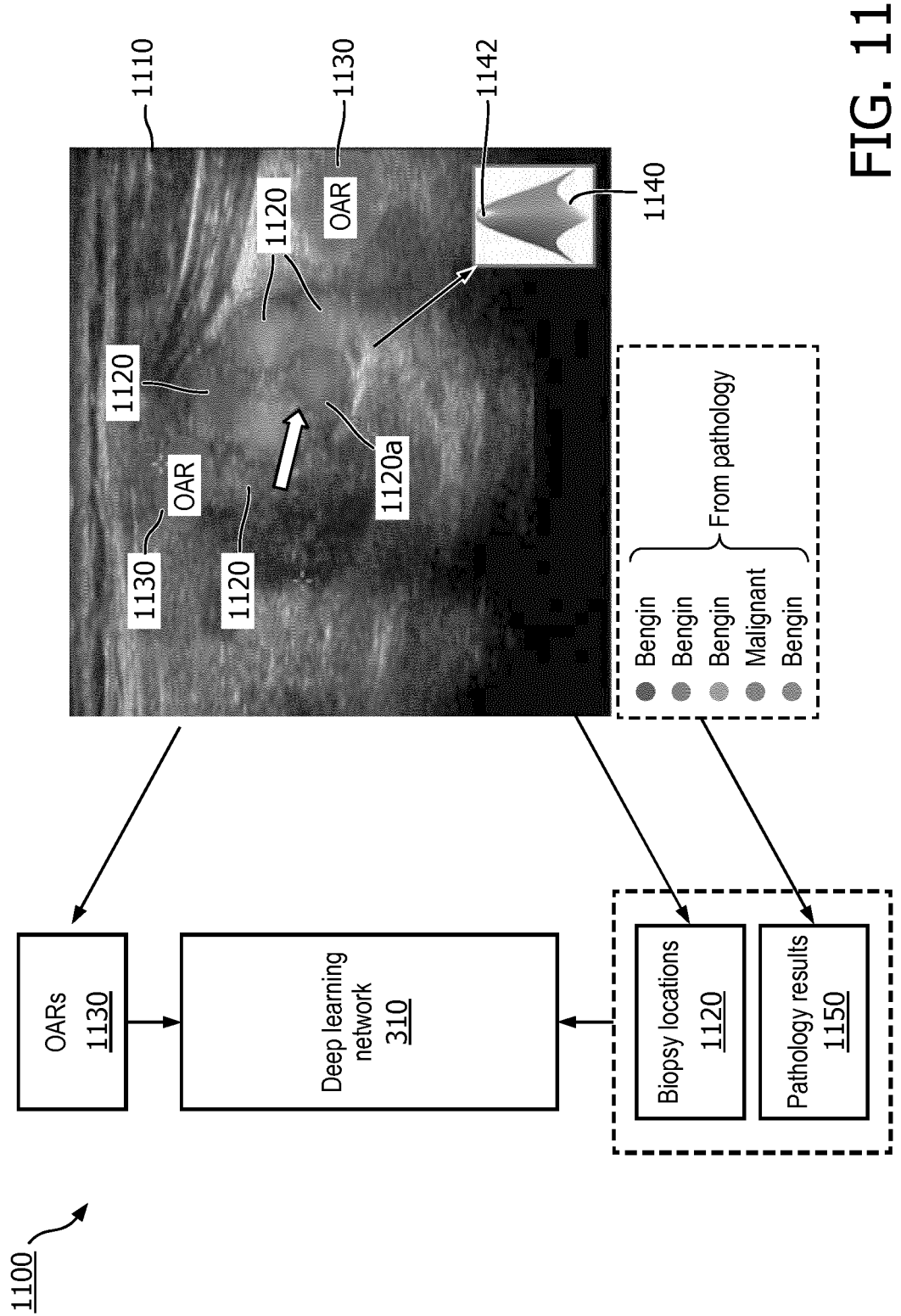
FIG. 11 is a schematic diagram illustrating a deep learning network training scheme, according to aspects of the present disclosure.

FIG. 11 is a schematic diagram illustrating a deep learning network training scheme 1100, according to aspects of the present disclosure. The scheme 1100 is implemented by the system 100. The scheme 1100 illustrates the training of the deep learning network 310 to predict a probability of malignancies for each pixel on an input image 302. To train the deep learning network 310, an annotated or labeled ultrasound image 1110 of tissues (e.g., including a thyroid) may be input to the deep learning network 310. The annotated ultrasound image 1110 may include one or more biopsy locations 1120 where biopsies were performed. Each biopsy location 1120 is shown as a closed surface shape. A malignancy certainty may be assigned to each biopsy location 1120 based on a corresponding pathology result 1150 obtained at the biopsy location 1120. The pathology result 1150 may indicate whether the tissue sample collected at the biopsy location 1120 is malignant, benign, or other (e.g., undetermined). In other words, the annotated ultrasound image 1110 includes a spatial malignancy certainty map for the underlying tissues captured by the image 1110.

The biopsy locations 1120 are discrete tissue locations and the pathology results 1150 are discrete result for corresponding biopsy locations 1120. In an embodiment, a 2D Gaussian function 1140 can be applied to the pathology result 1150 at each biopsy location 1120 to provide malignancy likelihood information with a higher spatial dimension. The peak 1142 of the Gaussian function 1140 may be mapped to the biopsy location 1120 where biopsy samples were taken. For example, the pathology result 1150 for the biopsy location 1120a is malignant. After applying the Gaussian function 1140 to the biopsy location 1120a, there is a highest certainty of malignancy (e.g., the peak 1142 of the Gaussian function 1140) at the biopsy location 1120 and the malignancy certainty decreases with an increasing space from the biopsy location 1120a. The rate at which the malignancy certainty decreases may depend on the variance of the Gaussian function 1140. The variance of the Gaussian function 1140 can be more conservative or less conservative depending on the size of the training data (e.g., the training data 140). For example, the Gaussian variance may be more conservative when there is a smaller amount of training data (e.g., the training data 140), but the resulting data labeling may have a greater certainty. On the other hand, the Gaussian variance may be less conservative when there is a greater amount of training data, but the resulting data labeling may have a less certainty. In general, the variance of the Gaussian function 1140 can be variable, for example, dependent on a biopsy location 1120. For example, correlations between a pathology sample taken at a given biopsy location 1120 and corresponding ultrasound imaging features can be learned to estimate an optimal variance for a Gaussian function 1140 at the given biopsy location 1120. In some instances, the variance of the Gaussian function 1140 can be user-defined during a training stage.

During training, the deep learning network 310 can be applied to the image 1110, for example, using forward propagation, to obtain an output or a score for each pixel on the image 1110, where the score may indicate a malignancy certainty or probability for the pixel. The coefficients of the filters 1022 in the convolutional layers 1020 and weightings in the fully connected layers 1030 can be adjusted, for example, by using backward propagation to minimize the output error. In other words, the coefficients in the convolutional layers 1020 and/or the weightings in the fully connected layers 1030 can be adjusted to match the pathology result 1150 at each of the biopsy locations 1120.

In an embodiment, the annotated ultrasound image1140 may further include annotations or labels for OARs 1130 (e.g., the OARs 410 and 912). Similarly, the deep learning network 310 can be applied to the image 1110, for example, using forward propagation, to obtain an output or a score for each pixel on the image 1110, where the score may indicate whether each pixel on the image 1110 corresponds to a critical area. The coefficients in the convolutional layers 1020 and/or the weightings in the fully connected layers 1030 can be adjusted to identify OARs at the locations of the annotated OARs 1130.

In an embodiment, the system 100 can be used to capture images of test tissues with malignancies and generate annotations for the images based on biopsy results. The system 100 may save the annotated images similar to the image 1110 as a training data set 140 in the memory 138. The scheme 1100 can be applied to train the deep learning network 310 using the training data set 140.

In an embodiment, similar training mechanisms as in the scheme 1100 may be used to train the deep learning network 310 to predict a biopsy target (e.g., the target biopsy location 340 and the biopsy target 620) from an input image (e.g., the images 302 and 1002) and/or a biopsy needle path (e.g., the biopsy needle paths 350, 610, and 940) to reach the predicted biopsy target from the input image. In such an embodiment, during training, the deep learning network 310 may be input with images annotated with OARs (e.g., the OARs 410 and 1130), biopsy locations (e.g., the biopsy locations 340, 913, and 1120), and biopsy needle paths (e.g., biopsy needle paths 350, 610, and 940) used for reaching corresponding biopsy locations.

In an embodiment, similar training mechanisms as in the scheme 1100 may be used to train the deep learning network 310 to predict a motion control configuration (e.g., the motion control configuration 820) for moving a probe (e.g., the probe 110) from a current position to an optimal imaging position for guiding a biopsy given an input image captured by the probe while the probe is at the current position. In such an embodiment, during training, the deep learning network 310 may be input with images of certain imaging planes, each associated with one or more motion control configurations used for manipulating a probe from an imaging plane of a corresponding image to an optimal imaging plane for guiding a biopsy to reach a biopsy location (e.g., the target biopsy locations 340 and the target biopsy 620). In an embodiment, the deep learning network 310 can be trained based on ultrasound images captured from multiple patients and/or multiple subjects. The deep learning network 310 can be trained using population-based training about the geometry of a thyroid (e.g., the thyroid 210) and surrounding critical structures or OARs to suggest an optimal imaging plane.

In some embodiments, the deep learning network 310 may include multiple CNNs 1010, for example, a first CNN 1010 may be trained to predict a probability of malignancies (e.g., the malignancy potential maps 320 and 400 and the confidence maps 330 and 500) for each pixel of an input image (e.g., the images 302 and 1002), a second CNN 1010 may be trained to predict a target biopsy location (e.g., the target biopsy location 340 and 620) and/or a biopsy needle path (e.g., the biopsy needle paths 350, 610, and 940), and a third CNN 1010 may be trained to predict a motion control configuration (e.g., the motion control configuration 820) for manipulating a probe (e.g., the probe 110) to reach an optimal imaging view (e.g., the imaging view 920) for guiding a biopsy.

Figure 12:
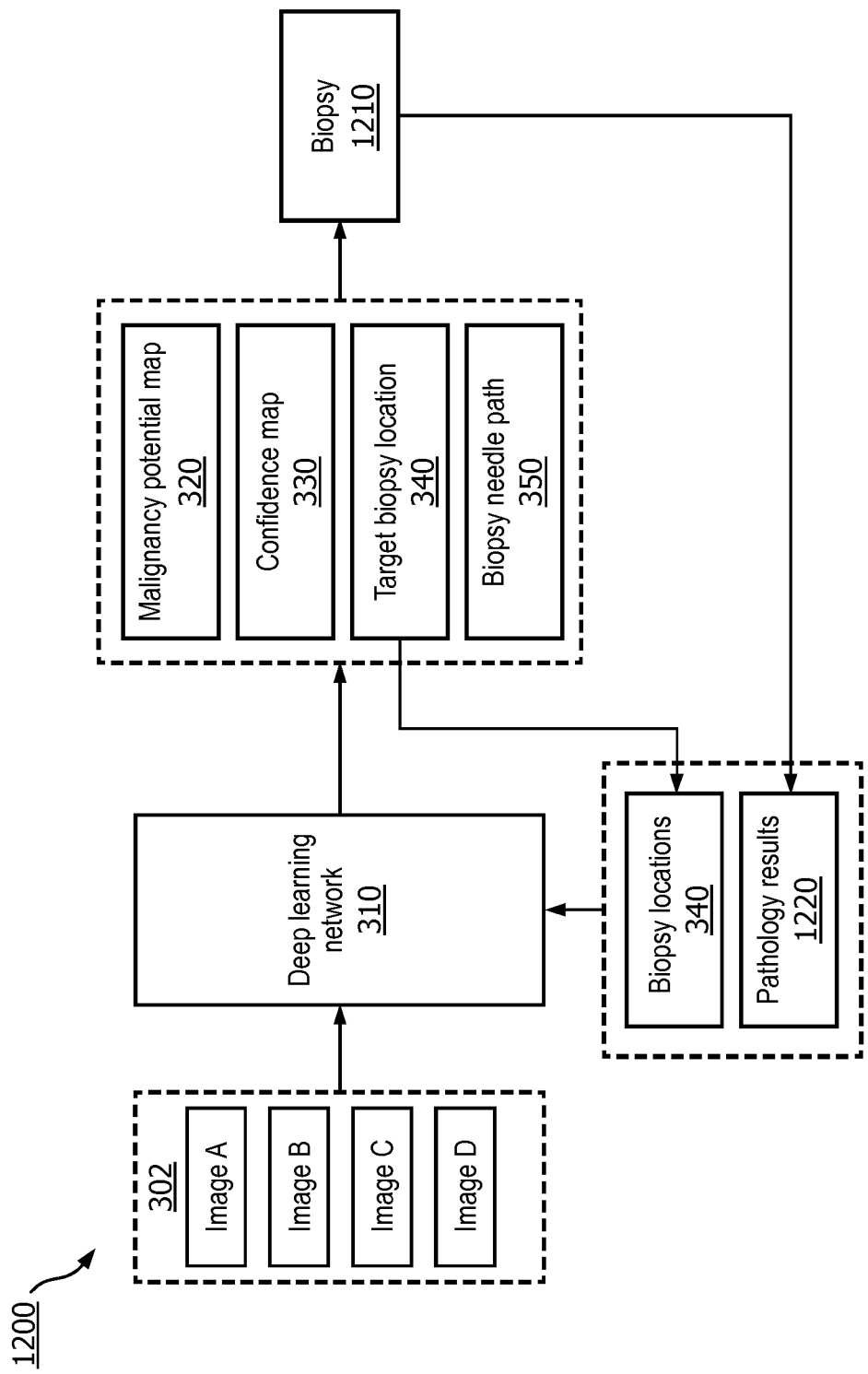
FIG. 12 is a schematic diagram illustrating a deep learning network fine-tuning scheme, according to aspects of the present disclosure.

FIG. 12 is a schematic diagram illustrating a deep learning network fine-tuning scheme 1200, according to aspects of the present disclosure. The scheme 1200 is implemented by the system 100. The scheme 1200 can be performed after obtaining a pathology result 1220 (e.g., the pathology result 1150) from a biopsy 1210 guided by the scheme 300. For example, a clinician may employ the deep learning network 310 in the scheme 300 to determine a target biopsy location 340. The clinician may perform a biopsy 1210 to collect tissue samples at the target biopsy location 340. Subsequently, a pathology result 1220 may be obtained from the collected tissue at the target biopsy location 340. The target biopsy location 340 and the corresponding pathology result 1220 may be fed back into the deep learning network 310 to fine-tune the deep learning network 310. The fine-tuning may include adjusting coefficients and/or weightings at the convolutional layers 1020 and/or at the fully connected layers 1030.

In some instances, the clinician may select a different biopsy location than the biopsy location 340 suggested by the deep learning network 310. The biopsy location selected by the clinician and the corresponding pathology result can also be fed into the deep learning network 310 to fine-tune the deep learning network 310.

The fine-tuning can be continuing process, for example, after each biopsy and when the pathology result is available. Accordingly, the fine-tuning can improve the prediction performance of the deep learning network 310.

Similarly, the fine-tuning can be applied to needle path prediction and/or imaging probe positioning prediction. For example, a biopsy needle path used to reach a target biopsy location for a biopsy and/or a movement used for manipulating a probe to reach an optimal imaging plane for guiding the biopsy can be fed back to the deep learning network 310 for the fine-tuning.

Figure 13:
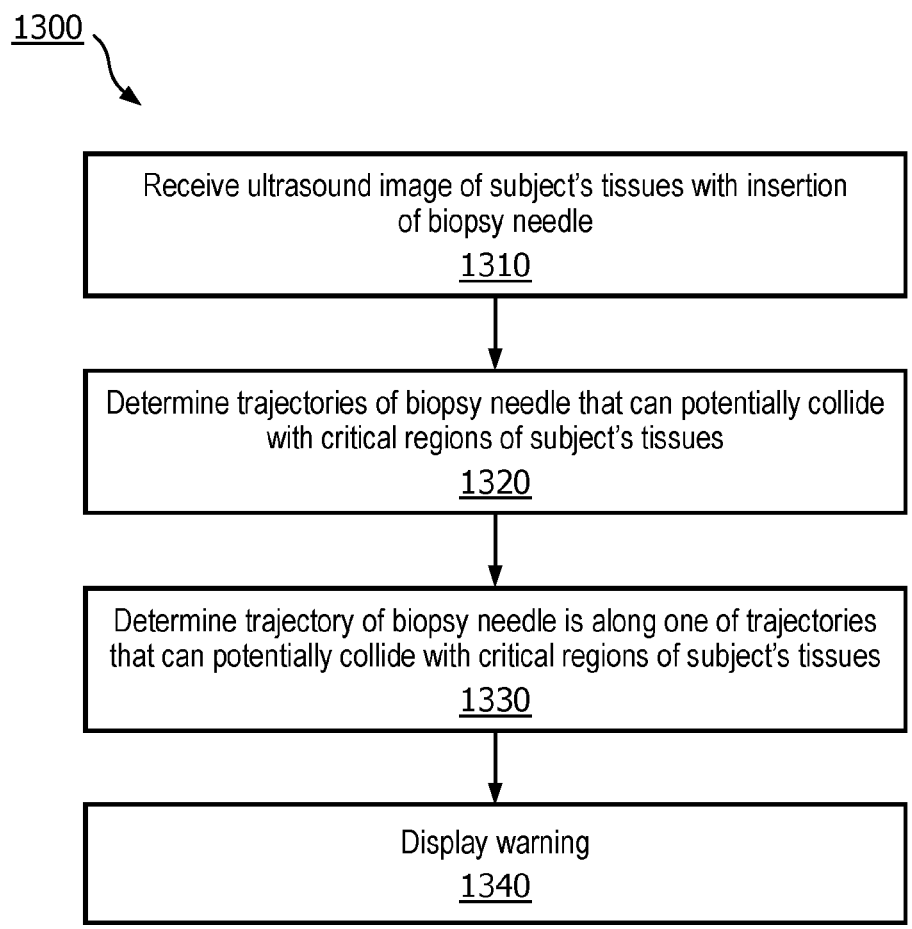
FIG. 13 is a flow diagram of a method of providing user warnings in a biopsy examination, according to aspects of the present disclosure.

FIG. 13 is a flow diagram of a method 1300 of providing user warnings in a biopsy examination, according to aspects of the present disclosure. Steps of the method 1300 can be executed by a computing device (e.g., a processor, processing circuit, and/or other suitable component) of a host such as the host 130. As illustrated, the method 1300 includes a number of enumerated steps, but embodiments of the method 1300 may include additional steps before, after, and in between the enumerated steps. In some embodiments, one or more of the enumerated steps may be omitted or performed in a different order. As described above, a clinician may determine a target biopsy location (e.g., the target biopsy location 340 and 620) for a biopsy examination on a patient's anatomy (e.g., a thyroid) based on a malignancy potential map (e.g., the malignancy potential maps 320 and 400) and a corresponding confidence map (e.g., the confidence maps 330 and 500). In some instances, the clinician may select a biopsy needle insertion point and/or a biopsy needle path to reach the target biopsy location. The method 1300 can be used to provide the clinician with warnings of intersecting a critical region (e.g., the OARs 410 and 912) of the patient's anatomy.

At step 1310, the method 1300 includes receiving an ultrasound image (e.g., the images 302 and 1002) representative of a patient's anatomy (e.g., the object 105) and an insertion of a biopsy needle.

At step 1320, the method 1300 includes determining possible trajectories of the biopsy needle that can collide with a critical region of the patient's anatomy.

At step 1330, the method 1300 includes detecting a trajectory of the biopsy needle is along one of the determined trajectories that can collide with a critical region of the patient's anatomy.

At step 1340, the method 1300 includes displaying a warning to the clinician based on the detection on a display (e.g., the display 132). For example, the warning can be in the form of a red light or any other suitable visual indicator on the display.

In an embodiment, the method 1300 can display all the determined trajectories that can collide with a critical region of the patient's anatomy on a display (e.g., the display 132). Upon detecting a trajectory of the biopsy needle along one of the trajectories, the method 1300 can highlight the detected trajectory and request the clinician to change the position of the entry point. Thus, the method 1300 can be used to change a user-selected biopsy needle path so that a biopsy can be performed safely.

Figure 14:
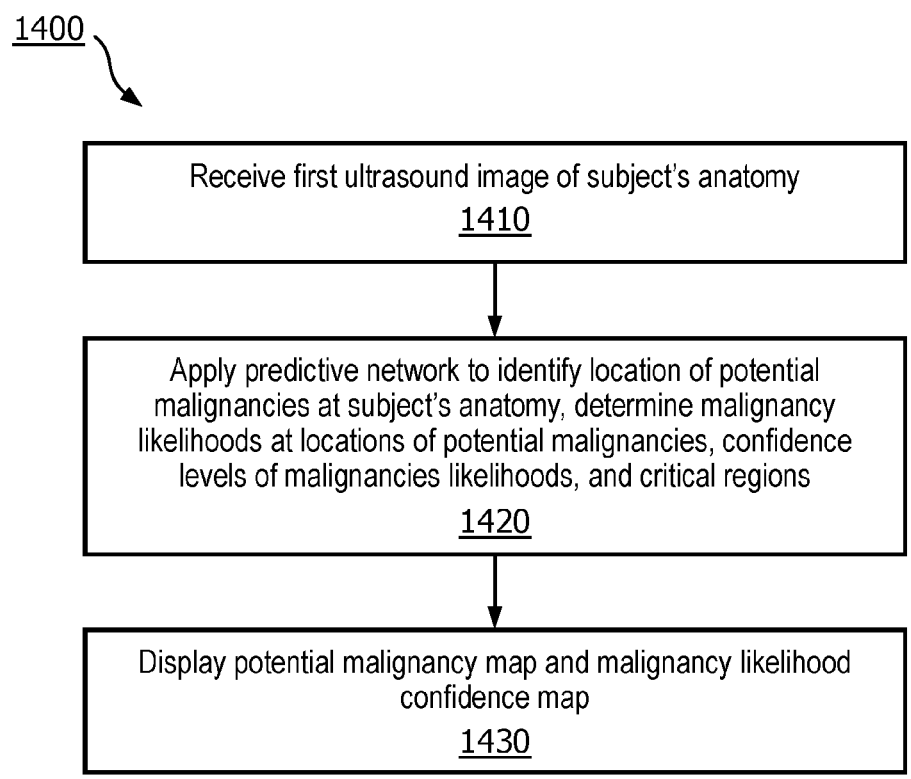
FIG. 14 is a flow diagram of a method of guiding a biopsy, according to aspects of the present disclosure.

FIG. 14 is a flow diagram of a method 1400 of guiding a biopsy, according to aspects of the present disclosure. Steps of the method 1400 can be executed by a computing device (e.g., a processor, processing circuit, and/or other suitable component) of an ultrasound imaging probe, such as the probe 110, or a host such as the host 130. The method 1400 may employ similar mechanisms as in the schemes 300, 800, 1100, and 1200, the configuration 1000, and the method 1300 described with respect to FIGS. 3, 8, 11, 12, and 10, respectively. As illustrated, the method 1400 includes a number of enumerated steps, but embodiments of the method 1400 may include additional steps before, after, and in between the enumerated steps. In some embodiments, one or more of the enumerated steps may be omitted or performed in a different order.

At step 1410, the method 1400 includes receiving, from an ultrasound imaging device (e.g., the probe 110), a first ultrasound image (e.g., the images 302 and 1002) of a subject's anatomy (e.g., the object 105).

At step 1420, the method 1400 includes applying a predictive network (e.g., the deep learning network 310) to the first ultrasound image to identify a plurality of locations (e.g., the locations 420 and 914) of potential malignancies in the subject's anatomy and determine a plurality of malignancy likelihoods at the plurality of locations of potential malignancies.

At step 1430, the method 1400 includes displaying, by a display (e.g., the display 132), the plurality of locations of potential malignancies and the plurality of malignancy likelihoods for the plurality of locations of potential malignancies to guide a biopsy determination for the subject's anatomy.

In an embodiment, the predict network can be applied to identify a critical region (e.g., the OARs 410 and 912) of the subject's anatomy to avoid for a biopsy determine a plurality of confidence levels for the plurality of malignancy likelihoods at the plurality of locations of potential malignancies. The display may include a first map (e.g., the malignancy potential maps 320, 400, and 600) and a second map (e.g., the confidence maps 330 and 500). The first map may include an overlay of indications of the plurality of locations of potential malignancies, the plurality of malignancy likelihoods, and the critical region on an instance (e.g., a copy or a version) of the first ultrasound image (e.g., as shown in FIG. 4). The second map may include an overlay of indications of the plurality of confidence levels on a different instance (e.g., a different copy or a different version) of the first ultrasound image corresponding to the plurality of locations of potential malignancies (e.g., as shown in FIG. 5). In some embodiments, the first map and the second map can be combined on the same instance of the first ultrasound image (e.g., using alpha-blending and/or other suitable image processing) to include an overlay of indications of the plurality of locations of potential malignancies, the plurality of malignancy likelihoods, the critical region, and the plurality of confidence levels on the first ultrasound image.

In an embodiment, the method 1400 may include determining a target biopsy location (e.g., the target biopsy locations 340 and 620) for performing a biopsy on the subject's anatomy based on at least one of the plurality of malignancy likelihoods at the plurality of locations of potential malignancies or the plurality of confidence levels for the plurality of malignancy likelihoods. The method 1400 may include determining a biopsy needle path (e.g., the biopsy needle paths 350, 610, and 940) for performing the biopsy based on at least one of the plurality of locations of potential malignancies, the critical region, or the target biopsy location of the subject's anatomy. The method 1400 may include displaying, by the display, the determined biopsy needle path as an overlay on the first map (e.g., as shown in FIG. 6).

In an embodiment the method 1400 may include determining that the critical region is along a trajectory path of a biopsy needle directed towards the subject's anatomy. The method 1400 may include displaying, by the display, an indication (e.g., a warning) of a potential collision between the biopsy needle and the critical region. In an embodiment, the trajectory path of the biopsy needle can be obtained from a second ultrasound image of the subject's anatomy with an insertion of the biopsy needle. In an embodiment, the trajectory path of the biopsy needle can be obtained from camera tracking, optical tracking, electromagnetic (EM) tracking, or any suitable tracking in an ultrasound image prior to insertion of the biopsy needle (e.g., after a user positioned the biopsy needle on the patient's skin, but prior to penetrating the patient's skin).

In an embodiment, the first ultrasound image is received while the ultrasound imaging device is positioned at a first imaging position with respect to the subject's anatomy. The method 1400 can include applying the predictive network to the first ultrasound image to determine a motion control configuration (e.g., the motion control configuration 820) for repositioning the ultrasound imaging device from the first imaging position to a second imaging position for performing the biopsy. The method 1400 may include displaying, by the display, a visual indicator (e.g., the visual indicator 902) for repositioning the ultrasound imaging device based on the motion control configuration.

Aspects of the present disclosure can provide several benefits. For example, the use of deep learning to automatically identify potential malignant locations and associated malignancy likelihoods and corresponding confidence levels and the displaying of the malignancy potential map and the confidence map can assist a clinician to determine the need for a biopsy and/or a target biopsy location. In addition, the use of deep learning to automatically suggest optimal biopsy needle paths, the displaying of the suggested biopsy needle paths, and/or the displaying of warning indications can guide a clinician performing a biopsy to reach a target biopsy location safely. Further, the use of deep learning to automatically suggest probe repositioning and the displaying of the suggested movements can guide a clinician to an optimal imaging view for performing a biopsy. The disclosed embodiments can allow a clinician to perform a successful biopsy without having many attempts (e.g., reaching a clinical allowable attempts), and thus may also reduce patient trauma. While the disclosed embodiments are described in the context of thyroid biopsy, the disclosed embodiments can be applied to guide biopsy in other parts of a body.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ultrasound imaging system comprising:
   an ultrasound imaging device; and
   a processor configured for communication with the ultrasound imaging device, wherein the processor is configured to:
      control the ultrasound imaging device to obtain an ultrasound image of a subject's anatomy during movement of a biopsy needle by a user through the subject's anatomy to perform a biopsy;
      provide the ultrasound image as an input to a predictive network;
      generate, as an output of the predictive network:
         a location of a potential malignancy in the subject's anatomy, wherein the potential malignancy is representative of an intended location for the biopsy needle during the movement; and
         a critical region of the subject's anatomy, wherein the critical region is representative of an anatomical structure of the subject that is different than the potential malignancy and is to be avoided by the biopsy needle during the movement; and
      provide, to a display in communication with the processor, guidance for the movement of the biopsy needle by the user through the subject's anatomy to the intended location while avoiding the critical region,
   wherein the guidance comprises:
      the ultrasound image; and
      a plurality of indications overlaid on the ultrasound image and comprising:
         a first indication that identifies the location of the potential malignancy; and
         a second indication that identifies the critical region and is distinct from the first indication, wherein the output of the predictive network is configured to cause the user to perform physical control of the biopsy needle for the biopsy needle to reach the location of the potential malignancy without the biopsy needle causing damage to the anatomical structure during the biopsy.

2. The system of claim 1, wherein the ultrasound image includes at least one of brightness-mode (B-mode) information, strain information, elasticity information, or tissue Doppler information.

3. The system of claim 1, wherein the processor is further configured to:
    determine, automatically, a biopsy needle path for performing the biopsy based on at least one of the location of the potential malignancy, the critical region, or a target biopsy location in the subject's anatomy.

4. The system of claim 3, further comprising:
    a user interface in communication with the processor and configured to receive a selection of the target biopsy location.

5. The system of claim 3, wherein the guidance comprises: the determined biopsy needle path as an overlay on the ultrasound image.

6. The system of claim 3, wherein the processor is further configured to apply the predictive network to the ultrasound image to determine the biopsy needle path.

7. The system of claim 3, wherein the processor is further configured to:
    determine that the critical region is along a trajectory path of the biopsy needle; and
    wherein the guidance comprises:
        an indication of a potential collision between the biopsy needle and the critical region.

8. The system of claim 3, wherein the ultrasound image is received while the ultrasound imaging device is positioned at a first imaging position with respect to the subject's anatomy, and wherein the processor is further configured to:
    apply the predictive network to the ultrasound image to determine a motion control configuration for repositioning the ultrasound imaging device from the first imaging position to a second imaging position for performing the biopsy; and
    wherein the guidance comprises: a visual indicator for repositioning the ultrasound imaging device based on the motion control configuration.

9. The system of claim 1, wherein the predictive network is trained by:
    providing a plurality of test ultrasound images of a test subject's anatomy, a biopsy location of a further biopsy performed on test subject's anatomy, and a pathology result of the further biopsy performed at the biopsy location; and
    assigning scores to pixels of the plurality of test ultrasound images based on the biopsy location and the pathology result.

10. The system of claim 1, wherein the subject's anatomy includes at least a portion of a thyroid.

11. The system of claim 10, wherein the intended location for the biopsy needle comprises at least one thyroid nodule, and
    wherein the critical region to be avoided by the biopsy needle comprises at least one of an internal jugular vein, a carotid artery, or a trachea.

12. The system of claim 1,
    wherein the processor is configured to apply the predictive network to the ultrasound image to:
        determine a malignancy likelihood at the location of the potential malignancy; and
        determine a confidence level for the malignancy likelihood, and
    wherein the plurality of indications further comprises:
        a third indication of the malignancy likelihood; and
        a fourth indication of the confidence level.

13. The system of claim 12, wherein the guidance comprises:
    a first map including the first indication identifying the location of the potential malignancy, the third indication of the malignancy likelihood, and the second indication identifying the critical region on a first instance of the ultrasound image; and
    a second map including the fourth indication of the confidence level at the location of the potential malignancy on a second instance of the ultrasound image.

14. The system of claim 12,
    wherein the processor is further configured to:
        determine, automatically, a biopsy needle path for performing the biopsy based on at least one of the location of the potential malignancy, the critical region, or a target biopsy location in the subject's anatomy; and
        determine the target biopsy location based on at least one of the malignancy likelihood at the location of the potential malignancy or the confidence level for the malignancy likelihood.

15. The system of claim 12, wherein the processor is further configured to:
    update the predictive network based on at least one of:
    a target biopsy location for the biopsy determined based on at least the location of the potential malignancy and the malignancy likelihood; or
    a pathology result of the biopsy.

16. A method of ultrasound imaging, comprising:
    controlling an ultrasound imaging device to obtain an ultrasound image of a subject's anatomy during movement of a biopsy needle by a user through the subject's anatomy to perform a biopsy;
    providing the ultrasound image as an input to a predictive network;
    generating, as an output of the predictive network:
        a location of a potential malignancy in the subject's anatomy, wherein the potential malignancy is representative of an intended location for the biopsy needle during the movement; and
        a critical region of the subject's anatomy, wherein the critical region is representative of an anatomical structure of the subject that is different than the potential malignancy and is to be avoided by the biopsy needle during the movement; and
    displaying, by a display, guidance for the movement of the biopsy needle by the user through the subject's anatomy to the intended location while avoiding the critical region,
    wherein the guidance comprises:
        the ultrasound image; and
        a plurality of indications overlaid on the ultrasound image and comprising:
            a first indication that identifies the location of the potential malignancy; and
            a second indication that identifies the critical region and is distinct from the first indication,
    wherein the output of the predictive network is configured to cause the user to perform physical control of the biopsy needle for the biopsy needle to reach the location of the potential malignancy without the biopsy needle causing damage to the anatomical structure during the biopsy.

17. The method of claim 16,
further comprising applying the predictive network to the ultrasound image to:
   determine a malignancy likelihood at the location of the potential malignancy; and
   determine a confidence level for the malignancy likelihood,
wherein the plurality of indications further comprises:
   a third indication of the malignancy likelihood; and
   a fourth indication of the confidence level.

18. The method of claim 17, wherein the displaying includes:
   displaying a first map including the first indication identifying the location of the potential malignancy, the third indication of the malignancy likelihood, and the second indication identifying the critical region on a first instance of the ultrasound image; and
   displaying a second map including the fourth indication of the confidence level on a second instance of the ultrasound image corresponding to the location of the potential malignancy.

19. The method of claim 18, further comprising:
   determining a target biopsy location for performing the biopsy based on at least one of the malignancy likelihood at the location of the potential malignancy or confidence level for the malignancy likelihood;
   determining a biopsy needle path for performing the biopsy based on at least one of the location of the potential malignancy, the critical region, or the target biopsy location; and
   displaying, by the display, the determined biopsy needle path as an overlay on the first map.

20. The method of claim 19, further comprising:
   determining that the critical region is along a trajectory path of the biopsy needle; and
   displaying, by the display, an indication of a potential collision between the biopsy needle and the critical region.

21. The method of claim 19, wherein the ultrasound image is received while the ultrasound imaging device is positioned at a first imaging position with respect to the subject's anatomy, and wherein the method further comprises:
   applying the predictive network to the ultrasound image to determine a motion control configuration for repositioning the ultrasound imaging device from the first imaging position to a second imaging position for performing the biopsy; and
   displaying, by the display, a visual indicator for repositioning the ultrasound imaging device based on the motion control configuration.

* * * * *